(12) United States Patent
Beachy et al.

(10) Patent No.: US 7,049,090 B2
(45) Date of Patent: May 23, 2006

(54) MODULATION OF HEDGEHOG-MEDIATED SIGNALING PATHWAY

(75) Inventors: Philip A. Beachy, Baltimore, MD (US); Ming-Jer Tsai, Houston, TX (US); Sophia Tsai, Houston, TX (US); Venkatesh Krishnan, Indianapolis, IN (US); Chien-Huan Chen, St. Louis, MO (US)

(73) Assignees: The Johns Hopkins University School of Medicine, Baltimore, MD (US); Baylor College of Medicine, Houston, TX (US)

(*) Notice: Subject to any disclaimer, the term of this patent is extended or adjusted under 35 U.S.C. 154(b) by 0 days.

(21) Appl. No.: 10/677,982

(22) Filed: Oct. 1, 2003

(65) Prior Publication Data

US 2004/0082036 A1    Apr. 29, 2004

Related U.S. Application Data

(63) Continuation of application No. 09/934,035, filed on Aug. 21, 2001, now Pat. No. 6,733,971, which is a continuation of application No. 09/023,249, filed on Feb. 13, 1998, now Pat. No. 6,277,566.

(51) Int. Cl.
*C12Q 1/48* (2006.01)
*C12Q 1/68* (2006.01)
*C12Q 1/02* (2006.01)
*G01N 33/53* (2006.01)

(52) U.S. Cl. .................. 435/15; 435/6; 435/7.8; 435/29

(58) Field of Classification Search ............ 435/6, 435/29, 7.8

See application file for complete search history.

(56) References Cited

U.S. PATENT DOCUMENTS

| 5,789,543 | A | 8/1998 | Ingham et al. .............. 530/350 |
| 5,844,079 | A | 12/1998 | Ingham et al. .............. 530/350 |
| 6,214,794 | B1* | 4/2001 | Beachy et al. ................ 514/12 |
| 6,261,786 | B1* | 7/2001 | Marigo et al. ............... 435/7.1 |

OTHER PUBLICATIONS

Frank Van Leeuwen et al, Letters To Nature, vol. 368, Mar. 1994.*
Zarkower et al, Cell, vol. 70: pp. 237-249, Jul. 24, 1992.*
Krishnan et al, Science, vol. 278: pp. 1947-1950, Dec. 1997.*
Ngo et al, The Protein Folding Problem and Tertiary Structure Prediction, Mertz et al (eds.), Birkhauser, Boston, pp. 433 and 492-495, 1994.*
Alexandre et al. "Transcriptional activation of hedgehog target genes in Drosophila is mediated directly by the *Cubitus interruptus* protein, a member of the GLI family of zinc finger DNA-binding proteins", Genes & Development, 10:2003-2013, (1996).
Krishnan et al., "Mediation of Sonic Hedgehog-Induced Expression of COUP-TFII by a Protein Phosphate", Science, 278:1947-1950 Dec. 12, 1997.
Marigo and Tabin, "Regulation of *Patched* by Sonic hedgehog in the developing neural tube", *Proc. Natl. Acad. Sci. . USA*, 93:9346-9351 (1996).
Zarkower and Hodgkin, Molecular Analysis of the *C. elegans* Sex-Determining Gene tra-1: A Gene Encoding Two Zinc Finger Proteins, Cell 70:237-249 Jul. 24, 1992.

* cited by examiner

*Primary Examiner*—Terry McKelvey
(74) *Attorney, Agent, or Firm*—DLA Piper Rudnick Gray Cary US LLP

(57) ABSTRACT

The present invention provides transcription factors associated with the hedgehog signaling pathway that are regulated by dephosphorylation by phosphatases. Hedgehog response elements (HRE) that interact with the dephosphorylated transcription factors are also provided as well as methods for identifying compounds that are phosphatase inhibitors. Methods of treating tumors in a subject by modulating the phosphorylation of the transcription factor are also included.

7 Claims, 20 Drawing Sheets

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 18 BASE PAIRS
        (B) TYPE: nucleic acid
        (C) STRANDEDNESS: both
        (D) TOPOLOGY: linear (ii) MOLECULE TYPE: genomic DNA (ix) FEATURE:
        (A) NAME/KEY:
        (B) LOCATION:

(xi) SEQUENCE DESCRIPTION: SEQ ID NO: 1:

GTTCTACATA ATGCGCCG                                                  18

(2) INFORMATION FOR SEQ ID NO: 2:

(i) SEQUENCE CHARACTERISTICS:
        (A) LENGTH: 18 BASE PAIRS
        (B) TYPE: nucleic acid
        (C) STRANDEDNESS: both
        (D) TOPOLOGY: linear (ii) MOLECULE TYPE: genomic DNA (ix) FEATURE:
        (A) NAME/KEY:
        (B) LOCATION:

(xi) SEQUENCE DESCRIPTION: SEQ ID NO: 2:

CGGCGCATTA TGTAGAAC                                              18

(2) INFORMATION FOR SEQ ID NO: 3:

(i) SEQUENCE CHARACTERISTICS:
        (A) LENGTH: 18 BASE PAIRS
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO: 3:

GTTCTACGTG ATGCGCCG                                              18

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO: 4:

TCCCGAAGAC CACCCACAAT GA                                         22

(2) INFORMATION FOR SEQ ID NO: 5:

(i) SEQUENCE CHARACTERISTICS:
        (A) LENGTH: 22 BASE PAIRS
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO: 5:

TCAAACCTAC TTTGGGGTCT TA                                         22

(2) INFORMATION FOR SEQ ID NO: 6:

(i) SEQUENCE CHARACTERISTICS:
        (A) LENGTH: 24 BASE PAIRS
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO: 6:

ATCGCCGGGG ATGAGCTGGC GGCT                                       24

-continued (2) INFORMATION FOR SEQ ID NO: 7:

(i) SEQUENCE CHARACTERISTICS:
        (A) LENGTH: 27 BASE PAIRS
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO: 7:

GATATGGCAA TGGTAGTCAG CACGTGG                  27

(2) INFORMATION FOR SEQ ID NO: 8:

(i) SEQUENCE CHARACTERISTICS:
        (A) LENGTH: 21 BASE PAIRS
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO: 8:

AGCTTCTCCA CTTGCTCTTG G                       21

MODULATION OF HEDGEHOG-MEDIATED SIGNALING PATHWAY

This application is a continuation application of U.S. application Ser. No. 09/934,035 filed Aug. 21, 2001, now issued as U.S. Pat. No. 6,733,971; which is a continuation application of U.S. application Ser. No. 09/023,249 filed Feb. 13, 1998, now issued as U.S. Pat. No. 6,277,566. The disclosure of each of the prior applications is considered part of and is incorporated by reference in the disclosure of this application.

BACKGROUND OF THE INVENTION

1. Field of the Invention

This invention relates generally to the field of regulation of gene expression, and more specifically to the modulation of transcription factors and genes in the hedgehog-mediated signaling pathway.

2. Description of the Related Art

Embryologists have long performed experimental manipulations that reveal the striking abilities of certain structures in vertebrate embryos to impose pattern upon surrounding tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families. One such family of proteins which may have an influential effect upon patterning activities are those proteins encoded by the hedgehog gene family.

The hedgehog (hh) gene was initially identified based on its requirement for normal segmental patterning in *Drosophila* (N_sslein-Volhard, C. & Wieschaus, E, *Nature* 287: 795–801, 1980). Its functions include local signaling to coordinate the identities of adjacent cells within early embryonic segments (Hooper, J. E., & Scott, M. P. *Early Embryonic Development of Animals*, pp. 1–48, 1992) and a later function in cuticle patterning that extends across many cell diameters (Heernskerk, J. & DiNardo, S., *Cell,* 76:449–460, 1994). The hh gene also functions in the patterning of imaginal precursors of adult structures, including the appendages and the eye (Mohler, J. *Genetics,* 120: 1061–1072, 1988; Ma, et al., *Cell,* 75:927–938, 1993; Heberlein, et al., *Cell,* 75:913–926, 1993; Tabata, T. & Kornberg, T. D., *Cell,* 76:89–102, 1992; Basler, K. & Struhl, G., *Nature,* 368:208–214, 1994). Genetic and molecular evidence indicates that hedgehog proteins are secreted and function in extracellular signaling (Mohler, J., supra; Lee, et al., *Cell,* 71:33–50, 1992; Taylor, et al., *Mech. Dev.,* 42:89–96, 1993).

In vertebrates, activities encoded by hh homologues have been implicated in anterior/posterior patterning of the limb (Riddle, et al., *Cell,* 75:1401–1416, 1993; Chang, et al., *Development,* 120:3339, 1994), and in dorsal/ventral patterning of the neural tube (Echelard, et al., *Cell,* 75:1417–1430, 1993; Krauss, et al., *Cell,* 75:1431–1444, 1993; Roelink, et al., *Cell,* 76:761–775, 1994).

In most of the embryonic tissues where Hedgehog signaling exerts a patterning effect, activation of the Hedgehog pathway is associated with a proliferative response in target cells. Such embryonic tissues include but are not limited to the developing neural tube, the presomitic mesoderm and the mesoderm of the developing limb bud. In addition, uncontrolled cell proliferation due to inappropriate activation of the Hedgehog signaling pathway is associated with formation of several tumor types including but not limited to basal cell carcinoma, medulloblastoma, and probably breast cancer and glioma. The uncontrolled proliferation in these tumors is probably due to the abnormal activation of transcription factors such as Gli1 that have a normal role in the Hedgehog signaling pathway. For example, in the case of basal cell carcinoma, all or nearly all cases are associated with inappropriately high level expression of the Gli1 transcription factor in basal keratinocytes (Dahmane et al., *Nature* 1997, 389(6653):876–881). Such inappropriate activation of Gli1 is thought to play a causal role in uncontrolled cell proliferation associated with basal cell carcinoma. The ability to modulate activity of such transcription factors thus represents a possible therapeutic approach to several clinically significant cancers.

The hedgehog polypeptide (HH) is synthesized as a precursor that undergoes autoprocessing to generate an amino-terminal fragment (HH-N) and a carboxy-terminus fragment (HH-C). Lee et al. *Science,* 266:1528–37, 1994. HH-N contains all the signaling activities of HH, whereas HH-C is responsible for the autoprocessing and attaches a cholesterol molecule to the carboxy-terminal of HH-N to regulate its spatial distribution. (Porter, J. A., et. al. *Nature,* 374:363–366, 1995. Porter, J. A., et. al. *Science,* 274: 255–259, 1996. Porter, J. A. et. al. *Cell,* 86:21–34, 1996).

SUMMARY OF THE INVENTION

The present invention is based on the seminal discovery that the hedgehog signaling pathway is regulated via a phosphorylated transcription factor in the hedgehog-mediated signaling pathway that undergoes dephosphorylation resulting in HH-mediated activation of target genes. Dephosphorylation of this transcription factor leads to increased binding to a hedgehog response element that is operatively associated with a target gene. Dephosphorylation of the transcription factor is mediated by a phosphatase.

In one embodiment, the invention provides an isolated transcription factor involved in a hedgehog-mediated signaling pathway. The transcription factor, which includes a phosphorylation site, is dephosphorylated in response to the hedgehog mediated signaling pathway which allows it to bind to a hedgehog response element. Preferably, the hedgehog response element is a sonic hedgehog response element (ShhRE) on a promoter for example. The sonic hedgehog response element contains the nucleic acid sequence 5'-GTT CTA CAT AAT GCG CCG-3' (SEQ ID NO:1) and the complementary sequence, 5'-CGG CGC ATT ATG TAG AAC-3' (SEQ ID NO:2).

In another embodiment, the invention includes a method for modulating expression of a target gene by modulating the phosphorylation of a transcription factor that interacts with a hedgehog response element operatively associated with the target gene. Preferably, the target gene is involved in a hedgehog signaling pathway, such as patched (ptc), the putative Shh receptor.

The phosphorylation of the transcription factor is modulated by affecting the activity of a phosphatase. Preferably, the modulation is inhibition of phosphatase signaling. In other preferred embodiments, the modulation is stimulation. Preferably, the phosphatase is a PP2A phosphatase or a phosphatase which can be inhibited by a PP2A phosphatase inhibitor, including okadaic acid or calyculin A for example.

The hedgehog signaling pathway may be any species of hedgehog, including the Drosophila, Zebrafish, Xenopus, chicken, murine or human hedgehog signaling pathway. In a preferred embodiment, the hedgehog signaling pathway is a vertebrate hedgehog signaling pathway, and more specifically, a human hedgehog signalling pathway.

The transcription factor of the invention may be a member of the Ci/Gli transcription factor family such as Cubitus interruptus (Ci) or Gli, or may be an unrelated transcription factor. The hedgehog response element may be a Ci-response element, a Gli-response element, or a sonic hedgehog response element for example.

In yet another embodiment, the present invention includes a method for treating a cell proliferative disorder in a subject. Examples of disorders that are likely targets for this type of treatment include but are not limited to basal cell carcinoma, medulloblastoma, and breast cancer, in all of which hedgehog pathway activation has been causally implicated. The method includes modulating hedgehog pathway activity by modulating activity of a phosphatase(s) that controls activity of transcription factors, such as Gli1.

In another embodiment, the invention includes a method for modulating proliferation or differentiation of neuronal cells. The method includes modulating phosphorylation of a transcription factor that binds to a hedgehog response element operatively associated with a target gene such as a gene that encodes a polypeptide that modulates proliferation or differentiation of the neuronal cells. For example, the target gene may encode COUP-TFII or a functional equivalent thereof.

The method may also include a step of detecting the proliferation or differentiation of the neuronal cells. Detecting includes assaying for the presence of a neuronal marker(s) including islet-1 (Isl-1), hepatocyte nuclear factor 3β (HNF3β) and/or SC-1 for example.

In yet another embodiment, the present invention includes a method for inhibiting bone defects by modulating the phosphorylation of a transcription factor that binds to a hedgehog response element, operatively associated with a target gene that encodes a polypeptide involved in mediating bone development.

In another embodiment, the present invention includes a method for diagnosing a hedgehog signaling pathway-mediated familial midline defect including determining the level of the phosphorylated transcription factor as compared to the level of dephosphorylated transcription factor. The transcription factor binds to a hedgehog response element in response to the hedgehog signaling pathway. The method also includes correlating the level of phosphorylated transcription factor as compared to the level of dephosphorylated transcription factor with the susceptibility for a familial midline defect, such as cyclopia or neural tube defect.

In another embodiment, the invention provides a method for identifying a compound which modulates phosphorylation of a transcription factor that functions in the hedgehog signalling pathway. The method includes incubating components comprising the compound, a PP2A phosphatase, and phosphorylated transcription factor under conditions sufficient to allow the components to interact and determining the effect of the compound on the phosphorylation state of the transcription factor before and after incubating in the presence of the compound. Compounds that affect dephosphorylation include peptides, peptidomimetics, polypeptides, chemical compounds and biologic agents. An exemplary compound described in the present examples is okadaic acid. The phosphorylation state of the transcription factor can be assayed using methodology as described in the present Examples (e.g., based on a shift in mobility).

In another embodiment, the invention provides a method for identifying a compound or small molecule which binds to or blocks transcription factor binding to HRE, thus blocking the HH signaling pathway. The method includes incubating components comprising the compound or small molecule(s), the HRE and either dephosphorylated transcription factor or phosphorylated transcription factor and phosphatase under conditions sufficient to allow the components to interact and measuring the effect on the HH signaling pathway.

BRIEF DESCRIPTION OF THE FIGURES

FIG. 7 shows the role of phosphatase and phosphatase inhibitors in Shh-N mediated signaling pathway.

DETAILED DESCRIPTION OF THE INVENTION

Figures 1A, 1B:
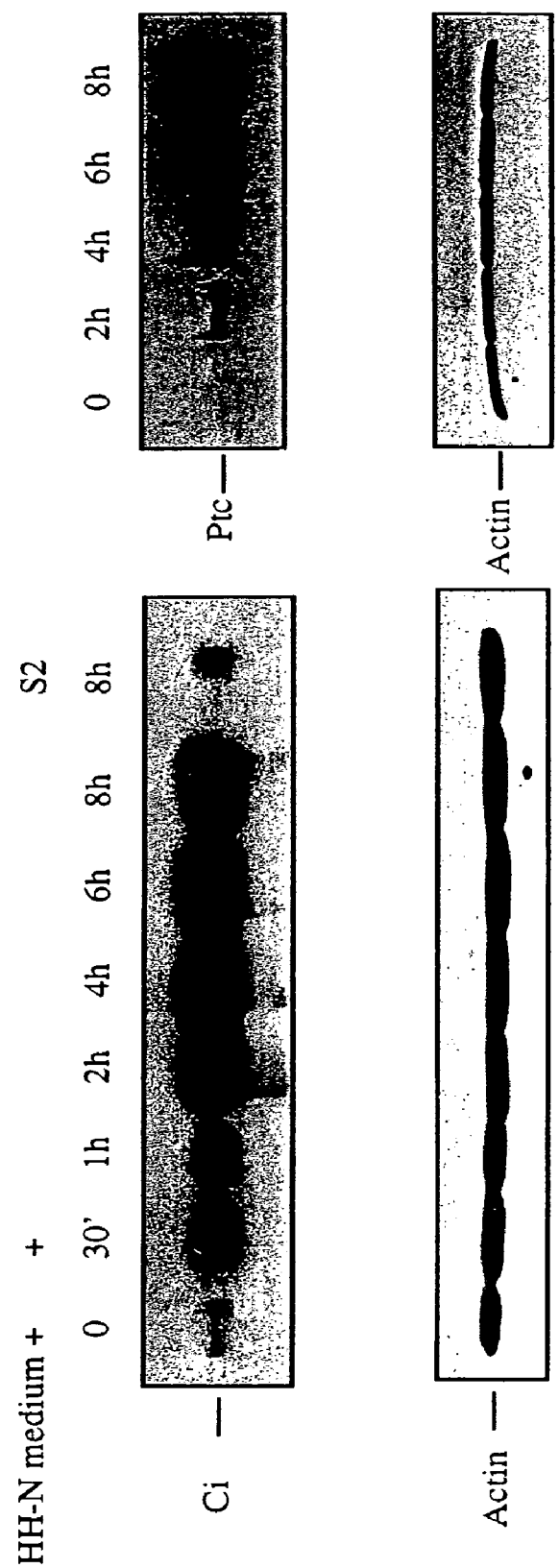
FIG. 1A shows the induction of Ci with HH-N conditioned medium.
FIG. 1B shows the induction of the Ptc polypeptide with HH-N conditioned medium.

The present invention is based on the finding that regulation of HH signaling is mediated by a phosphatase. Evidence is provided herein that the hedgehog-mediated signaling pathway leads to a change in the phosphorylation status of a transcription factor. Typically, the transcription factor is dephosphorylated in response to a hedgehog-mediated signaling pathway, with the dephosphorylation mediated by a phosphatase. The dephosphorylated transcription factor then binds to a hedgehog response element (HRE). The interaction of the transcription factor with the HRE leads to changes in the transcription of a target gene that is operatively associated with the HRE. Based on these observations, the invention provides methods that include modulation of the phosphorylation of the transcription factor, preferably by inhibition of an okadaic acid (OA) sensitive phosphatase.

In a first embodiment, the invention provides a transcription factor involved in a HH-mediated signaling pathway. "HH-mediated signaling pathway" as used herein refers to a signaling pathway that is activated by the HH polypeptide or the N-terminal fragment of HH polypeptide (HH-N) which is approximately 19 kD. The HH polypeptide or the HH-N polypeptide may be derived from a number of species including, without limitation, Drosophila, Zebrafish, Xenopus, chicken, murine or human. The HH polypeptide may be, for example, the Sonic hedgehog polypeptide (Shh), Indian hedgehog polypeptide (Ihh), Desert hedgehog (Dhh) or their amino-terminal fragments, Shh-N, Ihh-N, and Dhh-N, respectively (see Porter et al., *Nature* 374:363, 1995; Porter et al., *Science* 274:255, 1996, herein incorporated by reference). Accordingly, the HH-mediated signaling pathway may be the Shh-mediated signaling pathway, Ihh-mediated signaling pathway, Dhh-mediated signaling pathway, Shh-N-mediated signaling pathway, Ihh-N mediated signaling pathway, or Dhh-N-mediated signaling pathway.

The HH-mediated signaling pathway can include one or more molecules such as polypeptides and/or nucleic acids. The molecules in the signaling pathway may be altered in a number of ways in response to HH polypeptide. For example, molecules may be phosphorylated or dephosphorylated. Molecules may also undergo conformational changes and/or bind to other molecules. Thus, a variety of signals may be generated due to the presence of the HH polypeptide. Polypeptides involved in the HH-mediated signaling pathway may include, without limitation, kinases, phosphatases, and polypeptides that interact with nucleic acid sequences (e.g., transcription factors). Nucleic acid molecules involved in the HH-mediated signaling pathway may include, for example, polypeptide binding nucleic acid molecules.

In one embodiment, the invention includes an isolated transcription factor. The term "isolated" as used herein refers to a transcription factor that is substantially free of other proteins, lipids, carbohydrates, nucleic acids or other materials with which it is naturally associated. One skilled in the art can purify the transcription factor using standard techniques for protein purification. In one embodiment, the transcription factor is involved in the Shh-mediated signaling pathway and interacts with a response element such as the Shh-response element (ShhRE).

The invention includes a functional transcription factor and functional fragments thereof. As used herein, the term "functional transcription factor" or "functional fragment" refers to a transcription factor or a fragment of a transcription factor that possess the biological function or activity of interacting with the HRE. A functional assay may be used for identifying a transcription factor that is capable of interacting with the HRE. Such functional assays are exemplified in the Examples described herein. Functional fragments of the transcription factor include fragments of the transcription factor as long as the activity, e.g., interaction with the HRE, remains.

Minor modifications of the primary amino acid sequence of the transcription factor may result in polypeptides that have substantially equivalent activity as compared to the transcription factor activity described herein. Such modifications may be deliberate, as by site-directed mutagenesis, or may be spontaneous. All of the transcription factors produced by these modifications are included in the present invention as long as the transcription factor is capable of interacting with the HRE. Further, deletion of one or more amino acids can also result in a modification of the structure of the resultant molecule without significantly altering its activity.

The transcription factor of the present invention also includes conservative variations. The term "conservative variation" as used herein denotes the replacement of an amino acid residue by another biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The transcription factor may belong to one or more of the transcription factor families. Examples include zinc finger, helix-turn-helix, homeobox domain, SRY-box, amphipathic helix-loop-helix, leucine zipper and acid blob families. The transcription factor may be a member of the zinc finger family of transcription factors. The zinc finger family of transcription factors are polypeptides that include one or more atoms of zinc. In one embodiment, a transcription factor can include five to nine or more zinc atoms. Typically, each zinc atom is linked to about four amino acids in the polypeptide. The zinc atoms may be linked to cysteine and histidine amino acids in a polypeptide. For example, each zinc atom may be linked to two cysteines and two histidines. Alternatively, the zinc atoms may be linked to four cysteines. An example of a transcription factor that is a member of the zinc finger family of transcription factors is the polypeptide, Cubitus interruptus (Ci), or Gli (e.g., Gli1, Gli2, Gli3), the vertebrate homologs of Ci.

The transcription factor of the invention may include a homeobox domain. The homeobox domain is a sequence found in some polypeptides that may be involved in recognizing nucleic acid sequences in the target gene. Homeobox domains have been identified in a number of organisms including, for example, Drosophila and mice. The transcription factor may include a SRY-box, a sequence that is found in transcription factors that functions in determining important cell fates during differentiation (Pevny, L. H. et al., *Curr. Opinions in Gen. & Dev.* 7:338–344, 1997).

The transcription factor of the invention may contain a amphipathic helix-loop-helix motif. Each amphipathic helix presents a face of hydrophobic residues on one side and charged residues on the other side. The length of the connecting loop may vary from 12–28 amino acids.

The transcription factor of the invention may contain at least one leucine zipper motif. Leucine zipper includes a stretch of amino acids with a leucine residue in every seventh position. Positively charged amino acid residues may be present adjacent to the leucine zipper motif that can interact with a nucleic acid sequence.

The transcription factor of the invention may contain acid blobs. Acid blobs are non-specific amino acid sequences that can occur in polypeptides that interact with nucleic acid molecules and activate transcription of the target gene.

The transcription factor of the invention includes at least one phosphorylation site. The phosphorylation site can be phosphorylated transiently. Generally, the transcription factor is phosphorylated or dephosphorylated in response to the hedgehog-mediated signaling pathway. Hydroxyl-containing amino acids typically function as phosphorylation sites in polypeptides. For example, serine, threonine, and tyrosine contain amino acid side chains with hydroxyl groups that can be phosphorylated and dephosphorylated in response to appropriate signals. Phosphorylation at sites other than a serine, threonine or tyrosine are also within the scope of the invention.

The phosphorylation state of the transcription factor may be determined by an electrophoretic mobility shift assay (EMSA) or by SDS-PAGE as described in the Examples herein. For example, a mobility change accompanied the induction of Ci by the HH polypeptide (see Example 8). In the absence of the HH polypeptide, Ci was primarily in the lower mobility form, although the higher mobility form also existed in much lesser amount than the lower mobility form. Once HH polypeptide signaling began, the higher mobility form of Ci appeared with increased protein level.

The transcription factor of the present invention is capable of interacting and binding with an HRE. The HRE includes a nucleic acid molecule. Nucleic acid molecules that can be HREs include DNA, cDNA and RNA molecules that can interact with the transcription factor. The transcription factor may interact with the HRE in a sequence specific manner. In such a case, the transcription factor recognizes a particular nucleic acid sequence as the HRE. These nucleic acid sequences may be in the transcribed untranslated region of the target gene.

The invention also provides an isolated polynucleotide sequence that includes the HRE sequence. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences that contain the HRE sequence. It is understood that all polynucleotides containing the HRE are included herein, as long as they can interact with the transcription factor of the invention. Such polynucleotides include naturally occurring, synthetic, and intentionally manipulated polynucleotides. For example, the HRE may be subjected to site-directed mutagenesis. Also included in the invention are complementary fragments that selectively hybridize to the HRE.

Preferably the HRE is derived from a vertebrate organism, and most preferably from human. A number of HREs are known and include, without limitation, a Ci-response element (CiRE), a Gli-response element (GliRE), and sonic hedgehog response element (ShhRE). The ShhRE includes an AT rich motif followed by a GC core. Both the AT rich motif and the GC core can be involved in Shh-mediated signaling pathway. The ShhRE includes a TAAT motif that may be involved in interactions with the transcription factor. In preferred embodiments, the ShhRE includes the nucleic acid sequence 5'-GTT CTA CAT AAT GCG CCG-3' (SEQ ID NO:1). Variants of the ShhRE that can interact with the transcription factors described herein are also within the scope of this invention.

HREs of the invention include other response element nucleic acid sequences identified by hybridization to the HREs described herein. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Transcription factor nucleic acid sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences; and 2) PCR amplification of a desired nucleotide sequence using oligonucleotide primers.

Screening procedures which rely on nucleic acid hybridization make it possible to isolate any gene sequence from any organism, provided the appropriate probe is available. For example, oligonucleotide probe, which corresponds to all or a portion of the transcription factor can be synthesized chemically and used to probe libraries of other organisms using nucleic acid hybridization as described herein.

Among the standard procedures is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. The production of labeled single or double-stranded DNA or RNA probe sequences duplicating the HRE may be employed in DNA/DNA hybridization procedures which are carried out on cloned copies of the cDNA that have been denatured into a single-stranded form (Jay, et al., *Nucl. Acid Res.*, 11:2325, 1983).

A preferred method for obtaining genomic DNA, for example, is Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately $2^n$, where n is the number of cycles of amplification performed (see PCR Protocols, Eds. Innis, et al., Academic Press, Inc., 1990, incorporated herein by reference).

The present invention shows that the dephosphorylated transcription factor can increase the transcription of the target gene by binding to the HRE that is operatively associated with the target gene. Alternatively, the phosphorylated transcription factor can decrease or substantially inhibit the transcription of the target gene. The data in the present Examples of the invention demonstrate that dephosphorylation of the transcription factor is mediated by a phosphatase. Thus, in another embodiment, the invention includes a method for modulating expression of a target gene that includes modulating the phosphorylation of the transcription factor that binds to the HRE. The target gene to be modulated is operatively associated with the HRE.

The transcription factor can be any of the above-described transcription factors that include at least one phosphorylation site. The phosphorylation state of the transcription factor can be regulated by modulating the activity of a phosphatase that dephosphorylates the transcription factor. "Modulating" includes inhibiting or stimulating phosphatase activity. Other methods of dephosphorylating the transcription factor or phosphorylating the transcription factor may also be used for modulating the phosphorylation of the transcription factor and are within the scope of the invention. For example, the activity of a kinase that phosphorylates the transcription factor may also be modulated (e.g., cyclic-AMP-dependent protein kinase A (PKA), Fused (fu)).

The activity of a phosphatase can be inhibited to provide more of the transcription factor in the phosphorylated state. This can lead to a lower level of the dephosphorylated transcription factor that is available to interact with the HRE. For example, when HH is "misexpressed" or hyperactive, it may be desirable to use a phosphatase inhibitor to inhibit or decrease HH signaling.

Alternatively, the activity of a phosphatase can be increased. Increase in the phosphatase activity leads to a higher level of the dephosphorylated transcription factor. The higher level of dephosphorylated transcription factor results in greater availability of the dephosphorylated transcription factor to interact with the HRE. For example, where increased cell growth is desirable, it may be desirable to produce a hyperactive HH signaling pathway.

The modulation of the phosphorylation of the transcription factor can be performed in vitro, in vivo, or ex vivo. In one embodiment, the phosphatase may be added directly to the environment of the transcription factor. For example, if the transcription factor to be modulated is within a host cell, the phosphatase or a regulator of phosphatase activity may be microinjected into the cell. Alternatively, a phosphatase inhibitor, for example, can be administered. If the transcription factor is in a cell free environment, the phosphatase or a regulator of phosphatase activity may be added directly to the assay system.

The phosphatase may be expressed from a recombinant expression vector, either constitutively or transiently, for example, by the use of constitutive or inducible promoters, respectively. When the phosphatase is to be introduced into a host cell, the expression vector containing a nucleic acid sequence that encodes the phosphatase may be introduced and expressed in the host cell. The term "recombinant expression vector" refers to a plasmid, virus or other vehicle known in the art that has been manipulated by insertion or incorporation of a nucleic acid sequence. Such expression vectors contain a promoter sequence that facilitates the efficient transcription of a operatively associated polypeptide-encoding nucleic acid sequence. The expression vector typically contains an origin of replication, a promoter, as well as specific genes which allow phenotypic selection of the vector in transformed cells. Additional regulatory elements may also be present.

Methods that are well known to those skilled in the art can be used to construct expression vectors containing a phosphatase-encoding nucleic acid sequence and appropriate transcriptional/translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

If the recombinant expression vector needs to introduced into a host cell, transformation of the host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the target gene, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Different types of phosphatases are known in the art and can modulate the phosphorylation of the transcription factor in the present invention. The phosphatase may be a serine/threonine phosphatase. Phosphatase types include, without limitation, PP1, PP2A, PPIV, and PPV. In a preferred embodiment, the phosphatase is a PP2A phosphatase.

Different types of kinases are known in the art and may also be used to modulate the phosphorylation of the transcription factor. For example, cAMP activated protein kinase (PKA), inhibits the HH signaling pathway in Drosphila and vertebrates or fused (Fu), a novel serine/threonine kinase which positively acts in the HH signaling pathway, may be modulated.

The phosphorylation of the transcription factor may be modulated by inhibiting the phosphatase that dephosphorylates the transcription factor. A variety of phosphatase inhibitors are known and commercially available. The phosphatase inhibitor may be specific for inhibition of one phosphatase. Alternatively, the phosphatase inhibitor may inhibit a class of phosphatases, e.g. the PP2A phosphatases. The phosphatase inhibitor may also inhibit more than one type of phosphatase. In a preferred embodiment, the phosphatase inhibitor is a PP2A phosphatase inhibitor. Phosphatase inhibitors that can be used in the present invention include, without limitation, okadaic acid (OA) and Calyculin A (CyA). The phosphatase inhibitor may include a PPI inhibitor such as tautomycin (TAU). In in vivo uses, the phosphatase inhibitor may be administered systemically or locally. Preferably, the phosphatase inhibitor is administered locally.

The phosphorylation of the transcription factor may be modulated by increasing the phosphatase activity that dephosphorylates the transcription factor. For example, the phosphatase activity may be increased by activating the gene encoding the phosphatase, either the native phosphatase gene or the phosphatase gene in a recombinant expression vector. The phosphatase activity may also be increased by providing additional phosphatase polypeptide.

The HRE can be any of the above-described HREs and is operatively associated with the target gene. By "operatively associated", means a functional linkage between the HRE sequence and the target gene sequence. Thus, the HRE is positioned such that when the dephosphorylated transcription factor binds to the HRE, transcription of the target gene is controlled. Typically, when the dephosphorylated transcription factor binds to the HRE, the transcription of the target gene operatively associated with the HRE is increased. The HRE can be included within one of the regulatory elements of the target gene. Other regulatory elements associated with the target gene can include inducible and non-inducible promoters, enhancers, operators and other elements known to those skilled in the art and that drive or otherwise regulate expression of the target gene.

The HRE can be placed in a variety of locations in relation to the polypeptide-encoding portion of the target gene. For example, the HRE can be placed upstream or downstream of the polypeptide-encoding portion of the target gene, and can be located adjacent to, or at a distance from, the polypeptide-encoding portion of the target gene.

There may be one or more HREs operatively associated with the target gene. For example, in some of the experiments exemplified herein, three copies of the HRE were associated with the target gene. However, the presence of less than three functional copies of the HRE resulted in intermediate levels of transcription. If more than one HRE is present, the other HREs may or may not be the same HRE, i.e., a combination of HREs may be used. For example, the target gene may be operatively associated with two HREs, one of which is the ShhRE and the other the GliRE.

In the present invention, a target gene can be a gene that is naturally associated with the HRE. Alternatively, the target gene may be engineered to include the HRE. The HRE can be operatively associated with any gene of interest. The methods of the present invention can thus be utilized to have any gene of interest be responsive to modulation of the phosphorylation of the transcription factor involved in HH-mediated signaling pathway.

Target genes of the HH signaling pathway that are naturally associated with the HRE include patched (ptc), wingless (wg), and decapentaplegic (dpp) genes. These genes are naturally operatively associated with the CiRE. As demonstrated in examples below, the Ci level is increased by the HH signal, and a luciferase reporter under the control of ptc promoter is activated in a Ci-specific manner. Furthermore, it was found that Ci is less phosphorylated upon HH signaling, and the induction of Ci can be blocked by phosphatase inhibitor okadaic acid. Increased Ci level in the nucleus in the presence of HH signaling was also found.

The target gene may also be a gene in the Shh-signaling pathway. A gene in the Shh-signaling pathway can include, without limitation, a gene encoding COUP-TFII, a gene encoding Islet 1 (Isl1), a gene encoding hepatocyte nuclear factor 3β (HNF3β), and GliRE-dependent genes. Based on the Examples herein, transcription of these genes can be regulated by modulating the phosphorylation of the transcription factor.

The HRE may be genetically engineered into the target gene. Standard recombinant DNA techniques, site-directed mutagenesis and polymerase chain reaction may be used. Those of skill in the art can readily engineer the HRE into the target gene. A nucleic acid sequence including the HRE may be inserted in the target gene. Alternatively, the HRE may be created by mutagenizing one or more nucleotides in the target gene.

The target gene, with the operatively associated HRE, may be present in the genome of the host cell. Alternatively, the target gene operatively associated with the HRE may be present and expressed in the host cell from a recombinant expression vector. Recombinant expression vectors can be any of the vectors described herein. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The target gene can be present in the vector operably linked to regulatory elements, for example, a promoter (e.g., T7, metallothionein I, or polyhedrin promoters) in addition to the HRE.

A variety of host-expression vector systems may be utilized to express the target gene. These include but are not limited to microorganisms such as bacteria transformed with recombinant bacteriophage DNA, plasmid DNA or cosmid DNA expression vectors containing the target gene; yeast transformed with recombinant yeast expression vectors containing the target gene; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the target gene; insect cell systems infected with recombinant virus expression vectors (e.g., baculovirus) containing the target gene; or animal cell systems infected with recombinant virus expression vectors (e.g., retroviruses, adenovirus, vaccinia virus) containing the target gene, or transformed animal cell systems engineered for stable expression.

Depending on the host/vector system utilized, in addition to the HRE, any of a number of suitable transcription and translation elements, including constitutive and inducible promoters, transcription enhancer elements, transcription terminators, etc., may be used in the expression vector (see e.g., Bitter, et al., 1987, Methods in Enzymology, 153: 516–544). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted target gene. Promoter and regulatory elements that are naturally associated with the target gene may also be used in conjunction with the operatively associated HRE.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of the target gene.

A recombinant expression vector containing the target gene can be introduced and expressed in vitro by DNA transfer into a suitable host cell. "Host cells" are cells in which a vector can be propagated and its DNA expressed.

The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

Hosts cells can include, without limitation, microbial, yeast, insect and mammalian host cells. Methods of expressing DNA sequences having eukaryotic or viral sequences in prokaryotes are well known in the art. Biologically functional viral and plasmid DNA vectors capable of expression and replication in a host are known in the art, as well as methods that can be used to construct expression vectors containing the target genes described herein. Mammalian cell lines may be preferable. Host cell lines may include but are not limited to S2, cl-8, and P19, CHO, VERO, BHK, HeLa, COS, MDCK, -293, and WI38.

Target genes may be expressed in cells that contain a HH-mediated signaling pathway or target genes may also be expressed in cells that do not naturally contain any of the transcription factors described herein by introducing an exogenous source of the transcription factor. The exogenous source of transcription factor may be phosphorylated or dephosphorylated prior to introduction into the host cell.

Host cells can be transformed with the target gene controlled by appropriate expression control elements (e.g., promoter, enhancer, sequences, transcription terminators, polyadenylation sites, etc.), and a selectable marker. Transformation may be performed by the methods described above and other methods known in the art. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11: 223, 1977), hypoxanthine-guanine phosphoribosyltransferase (Szybalska and Szybalski, *Proc. Natl. Acad. Sci. USA*, 48:2026, 1962), and adenine phosphoribosyltransferase (Lowy, et al., *Cell*, 22: 817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Natl. Acad. Sci. USA*, 77: 3567, 1980; O'Hare, et al., *Proc. Natl. Acad. Sci. USA*, 78: 1527, 1981); gpt, which confers resistance to mycophenolic acid (Mulligan and Berg, *Proc. Natl. Acad. Sci. USA*, 78: 2072, 1981; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30:147, 1984) genes. Recently, additional selectable genes have been described, namely trpB, which allows cells to utilize indole in place of tryptophan; hisD, which allows cells to utilize histinol in place of histidine (Hartman and Mulligan, *Proc. Natl. Acad. Sci. USA*, 85:8047, 1988); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

In another embodiment, the present invention includes a method for modulating proliferation or differentiation of neuronal cells. Previous studies in mice have shown that COUP-TFI and COUP-TFII are expressed in the neural tube during embryonic development. COUP-TFII was highly expressed and displayed a restricted expression pattern that was coincident with motor neuron differentiation (Tsai et al. *Endocrine Reviews* 18:229–240, 1997). Transplantation of a notochord to the dorsal side of the chick neural tube resulted in ectopic COUP-TFII expression that coincides with the appearance of motor neuron markers, such as Isl1 and SC-1 in these regions (Lutz, B., et al. *Development* 120:25–36, 1994). Based on the Examples herein, which demonstrate the role of phosphatase in the dephosphorylation of the transcription factor and the interaction of the dephosphorylated transcription factor with the ShhRE on the gene encoding COUP-TFII, the proliferation or differentiation of neuronal cells can be regulated by modulating the phosphorylation of the transcription factor involved in interacting with the ShhRE.

Preferably, the neuronal cells to be modulated are vertebrate neuronal cells and most preferably, human neuronal cells. Preferably, the modulation is induction of proliferation or differentiation of the neuronal cells. The neuronal cells may be induced by increasing the amount of phosphatase available to dephosphorylate the transcription factor, thus increasing the level of the dephosphorylated transcription factor and increasing HH signaling. Alternatively, the amount of dephosphorylated transcription factor may be decreased by inhibiting the phosphatase, thus negatively modulating the induction of the proliferation of neuronal cells by decreasing HH signaling.

The HRE is preferably operatively associated with a target gene. The target gene may be any of the above-described target genes that includes a nucleic acid sequence that encodes a polypeptide involved in modulating proliferation or differentiation of neuronal cells. Preferably, the HRE is a ShhRE described herein.

In preferred embodiments, the target gene is the gene encoding COUP-TFII. In other preferred embodiments, the interaction of the dephosphorylated transcription factor with the HRE leads to changes in the expression of neuronal markers Isl1, HNF3β and SC-1. Thus, the method may include a step of detecting the proliferation or differentiation of the neuronal cells. Proliferation or differentiation of neuronal cells may be detected by assaying for the presence of a neuronal marker. As such, Isl1, HNF3β and/or SC-1 may be used as neuronal markers for detecting the proliferation or differentiation of neuronal cells. Other markers indicating proliferation or differentiation may also be used. Neuronal markers may be assayed by a variety of techniques including, without limitation, Western blot analysis and Northern blot analysis.

In yet another embodiment, the present invention includes a method for treating a cell proliferative disorder in a subject. Examples of disorders that are likely targets for this type of treatment include but are not limited to basal cell carcinoma, medulloblastoma, and breast cancer, in all of which hedgehog pathway activation has been causally implicated. The method includes modulating the phosphorylation of a transcription factor that interacts with a hedgehog response element by administering to the subject a modulating effective amount of a phosphatase inhibitor. The method includes modulating hedgehog pathway activity by modulating activity of a phosphatase(s) that controls activity of transcription factors, such as Gli1. Further, the response element is preferably operatively associated with a target gene, such as the ptc gene.

Various cell proliferative disorders or tumors that can be treated using the method of the invention include basal cell carcinoma (BCC), medulloblastoma, and meningiomas. Basal cell nevus syndrome (BCNS, also called Gorlin syndrome), characterized by developmental abnormalities and by the postnatal occurrence of cancers, especially BCC, is due to a mutation in the human homolog of the Drosophila ptc gene. Thus, proper expression of ptc, which is also regulated by the HH signaling pathway, is associated with proper embryonic development and tumor suppression. Accordingly, inhibition of a phosphatase in the HH signaling pathway, as described herein, may be useful in inhibiting or ameliorating such tumors as BCC. Preferably, treatment is by local administration of a pharmaceutical composition containing a phosphatase inhibitor, e.g., okadaic acid.

Phosphatase inhibitors are administered by any suitable means, including parenteral, subcutaneous, intrapulmonary, and intranasal administration. Parenteral infusions include intramuscular, intravenous, intraarterial, or intraperitoneal administration. Phosphatase inhibitors can also be administered by inhalation.

Phosphatase inhibitors may also be administered transdermally in the form of a slow-release cutaneous or subcutaneous implant for example, or orally in the form of capsules powders or granules. Phosphatase inhibitors may also be applied locally directly on the epidermis (e.g., topically), in the form of a cream or ointment, for example, in the case of BCC. A carrier may comprise any one of conventional topical formulation bases such as those described in Remington's "Pharmaceutical Sciences," 17th Edition (Mack Publishing Co., Pa). A lotion, solution, cream, gel, ointment, paste, aerosol, suppository, and nebulized formulation are representative of the topical compositions useful in the method of this invention.

Additional ingredients may be added to the topical composition, as long as they are pharmaceutically acceptable and not deleterious to the epithelial cells or their function. Further, they should not adversely affect the epithelial penetration efficiency of the composition such as the phosphatase inhibitor, and should not cause deterioration in the stability of the composition. For example, fragrances, opacifiers, antioxidants, gelling agents, stabilizers, surfactants, emollients, coloring agents, preservatives, buffering agents, and the like may be present. The pH of the topical composition of this invention may be adjusted to a physiologically acceptable range of from about 6.0 to about 9.0 by adding buffering agents thereto in order for the composition to be physiologically compatible with the skin.

Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients which are pharmaceutically acceptable and compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention provides any pharmaceutical preparations and compositions containing the phosphatase inhibitors of the invention for use in the method of the invention. The form will vary depending upon the route of administration. For example, compositions for injection can be provided in the form of an ampule, each containing a unit dose amount, or in the form of a container containing multiple doses.

Phosphatase inhibitors can be formulated into the therapeutic composition as neutralized pharmaceutically acceptable salt forms. These include the acid addition salts which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the phosphatase inhibitors may be controlled by altering the concentration of the macromolecule.

Another method for controlling the duration of action comprises incorporating the phosphatase inhibitors into particles of a polymeric substance such as polyesters, polyamino acids, hydrogels, polylactide/glycolide copolymers, or ethylenevinylacetate copolymers. Alternatively, it is possible to entrap phosphatase inhibitors in microcapsules prepared, for example, by coacervation techniques or by interfacial polymerization, for example, by the use of hydroxymethylcellulose or gelatin-microcapsules or poly (methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The dosage range for administration of phosphatase inhibitors will vary depending on the age, sex, and physical condition of the subject. Phosphatase inhibitors is administered from about 1 to about 100 µg\100 g\dose, preferably from about 1 to about 50 µg\100 g\dose, and most preferably from about 1 to about 20 µg\100 g\dose.

In another embodiment, the invention includes a method for inhibiting or blocking bone defects in a subject. The method includes modulation of the phosphorylation of the transcription factor that interacts with the HRE that is operatively associated with a target gene. The target gene may be any of the above-described target genes that encodes a polypeptide that mediates bone formation and/or bone maintenance. Examples of bone or skeletal defects include polydactyly, jaw and rib defects, and spina bifida.

In yet another embodiment, the invention includes a method for diagnosing a HH-signaling pathway mediated familial midline defect in a subject. Defects in the HH autoproteolysis may be responsible for the defects. Deficiencies in the HH leads to an abnormal HH-signaling pathway that can result in abnormal levels of phosphorylated and/or dephosphorylated transcription factor. The level of dephosphorylated transcription factor and phosphorylated transcription factor can be determined as described in the Examples herein. Appropriate cells include neuronal cells and other cells that are mediated by HH-signaling pathway. The ratio of the dephosphorylated transcription factor to the phosphorylated transcription factor can be calculated. In some embodiments, the ratio may be greater than the normal value and in other embodiments, the ratio may be smaller than the normal value. The defects that may be diagnosed include, without limitation, cyclopia and neural tube defects.

In another embodiment, the invention provides a method for identifying a compound which modulates phosphorylation of a transcription factor that functions in the hedgehog signalling pathway. The method includes incubating components comprising the compound, a PP2A phosphatase, and phosphorylated transcription factor under conditions sufficient to allow the components to interact and determining the effect of the compound on the phosphorylation state of the transcription factor before and after incubating in the presence of the compound. Compounds that affect dephosphorylation include peptides, peptidomimetics, polypeptides, chemical compounds and biologic agents. An exemplary compound described in the present examples is okadaic acid. The phosphorylation state of the transcription factor can be assayed using methodology as described in the present Examples (e.g., based on a shift in mobility SDS-PAGE or (EMSA)).

Incubating includes conditions which allow contact between the test compound and the phosphatase and transcription factor. Contacting includes in solution and in solid phase, or in a cell. The test compound may optionally be a combinatorial library for screening a plurality of compounds.

In another embodiment, the invention provides a method for identifying a compound or small molecule which binds to or blocks transcription factor binding to HRE, thus blocking the HH signaling pathway. The method includes incubating components comprising the compound or small molecule(s), the HRE operatively associated with a target gene and either dephosphorylated transcription factor or phosphorylated transcription factor and phosphatase under conditions sufficient to allow the components to interact and measuring the effect on the HH signaling pathway. Compounds or small molecule(s) that bind to either the transcription factor or HRE, or block the interaction, include peptides, peptidomimetics, polypeptides, chemical compounds and biologic agents. HH signaling can be determined by an in vitro assay, such as described in the Examples (e.g., mobility shift assays (EMSA)). Incubating includes conditions which allow contact between the test compound or small molecule(s) and the other components. Contacting includes in solution and in solid phase.

In addition to mobility shift assays, as described herein, other assays can be performed to determine if a compound or small molecule(s) can functionally complex with the transcription factor, HRE or both, or if a compound is a phosphatase inhibitor. Induction of an exogenous or endogenous gene can be monitored by monitoring changes in the protein levels or mRNA levels, for example. When a compound or small molecule(s) is found that can reduce Shh-induced increase in CAT mRNA, for example, it is concluded that this compound or small molecule(s) can bind to or block the transcription factor binding to HRE, or block the phosphatase required for dephosphorylation of the transcription factor.

Expression of the exogenous gene (e.g., CAT) can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol cetyl-transferase gene, an alkaline phosphatase gene, beta-galactosidase, a luciferase gene, a green fluorescent protein gene, guanine xanthine phosphoribosyltransferase, alkaline phosphatase, and antibiotic resistance genes (e.g., neomycin phosphotransferase). The compound or small molecule(s) of the present invention can be extracted and purified from the culture media or a cell by using known protein purification techniques commonly employed, such as extraction, precipitation, ion exchange chromatography, affinity chromatography, gel filtration and the like. Compound or small molecule(s) can be isolated by affinity chromatography using the modified receptor protein extracellular domain bound to a column matrix or by heparin chromatography.

Also included in the screening method of the invention are combinatorial chemistry methods for identifying small molecule or chemical compounds that affect HH signaling pathways. The screening method is also useful for identifying variants, binding or blocking agents, etc., which functionally, if not physically (e.g., sterically) act as antagonists or agonists, as desired.

The following examples are intended to illustrate but not limit the invention. While they are typical of those that might be used, other procedures known to those skilled in the art may alternatively be used.

EXAMPLES

Example 1

Effects of HH-N Conditioned Medium

Methods

Cell Culture and Cell Lysate cl-8 cells were cultured as described in Van Leeuwen, F., et al. *Nature*, 368:342–344, 1994. Culture and transfection of S2 cells were performed as described in Porter, J. A. et al. *Cell*, 86: 21–34, 1996. The conditioned medium was made by culturing transfected S2 cells in cl-8 medium, and induced by adding $CuSO_4$ to the final concentration of 0.5 Mm overnight. The conditioned medium was harvested the next day, centrifuged to remove S2 cells and the supernatant was used. To make lysate from cl-8 cells, cl-8 cells were washed, harvested in cold phosphate buffered saline (PBS), and then resuspended in NP-40 lysis buffer (150 Mm NaCl, 50 Mm Tris pH8, 1% NP-40, 1 Mm EDTA, 20 µg/ml aprotinin, 20 µg/ml leupeptin, 1 µg/ml pepstatin A, 2.5 µg/ml antipain, 100 µM PMSF, 50 mM NaF, 5 mM $Na_2P_4O_7$). Cells were lysed at 4° C. for 10 minutes, then centrifuged at 13,000×g for 10 minutes. The supernatant was saved for Western blot analysis.

Western Blot Analysis

SDS-PAGE and protein transfer were carried out by standard methods. The primary antibodies used were: rat monoclonal anti-Ci 2A1 1:20 dilution; mouse monoclonal anti-Ptc 1:1000 dilution; mouse monoclonal anti-actin 1:2500. Secondary antibodies were from Jackson Immunologicals. The filters were developed using SuperSignal from Pierce.

Northern Blot Hybridization

RNA was isolated from cl-8 cells using TRIzol (Gibco-BRL) and the concentration of the sample was determined by OD260. 25 µg of each sample was loaded and the procedure was as described in Ausubel, F. M. et al. *Current protocols in molecular biology*, John Weily & Sons Inc., New York, 1994. The probes for ci and ptc were generated by polymerase chain reaction (PCR), corresponding to the region of ci 2387–3195 and ptc 2298–3113. The probe of RP49 was a gift from D. Andrew constructs (DAK).

Reporter Constructs and Assay cl-8 cells were transfected by the calcium phosphate method and incubated overnight. 1 µg of the reporter, 25 ng of pRL-CMV and 9 µg of carrier DNA were used per 6 cm plate of cl-8 cells. The transfected cells were washed with fresh medium and the next day and incubated with conditioned medium overnight. The cells were lysed in Passive Lysis Buffer (Promega) for 15 minutes, and spun for 10 minutes at 13,000×g. The supernatant was assayed by luminometer according to manufacturer's instruction.

Results

Schneider (S2) cells were transfected with HH-N under the control of metallothionine promoter for inducible expression and secretion of HH-N into the cell culture medium. Since soluble HH protein was not available, the conditioned medium containing the HH-N (the HH-N conditioned medium) was used as the source of HH signaling and the conditioned medium harvested from S2 cells (the S2 conditioned medium) without transfection was used as a control.

cl-8 cells were incubated with either the HH-N or S2 conditioned medium for various periods of time and the Ci protein level was analyzed. After treatment with the HH-N conditioned medium, the Ci protein level was induced by 30 minutes (FIG. 1A), and continued to increase until it reached a plateau after 4 to 6 hours of treatment. On the other hand, Ci protein level was not changed when treated with the S2 conditioned medium for 8 hours. The protein level of Ptc, in contrast, did not elevate until 4 hours after treatment with the HH-N conditioned medium (FIG. 1B).

Figure 1C:
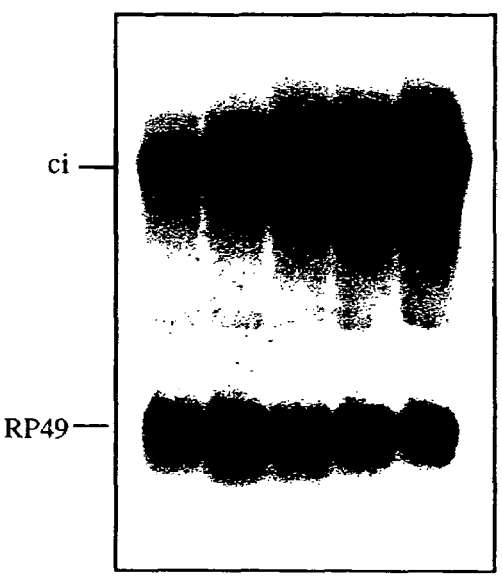
FIG. 1C and FIG. 1D show transcription of the ci and ptc genes, respectively.
Figure 1D:
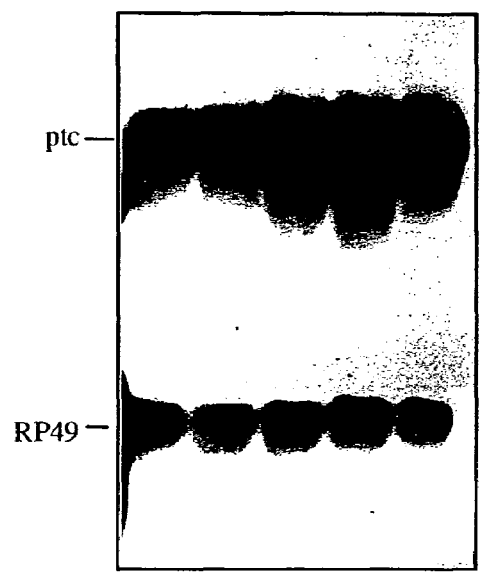

The transcriptions of the ci gene and ptc gene were analyzed by Northern blot hybridizations (FIG. 1C and FIG. 1D). It was found that both ci and ptc transcription remained stable in the first 4 hours but started to increase after 4 hours. Since an increase in Ci protein level was seen by 30 minutes, long before the transcription of ci started to rise, the increased Ci protein level must be due to a posttranscriptional mechanism. After 4 hours of treatment with HH-N, the increase of the Ci protein level can be due to a transcriptional or posttranscriptional mechanism. The parallel change in the transcription and the protein level of ptc suggests that the induction of the Ptc protein by HH signaling resulted from the increase of the ptc transcription.

Example 2

Induction of Luciferase Using a Ptc Promoter

A luciferase reporter under the control of the ptc promoter from +130 to −758 was constructed and transfected into cl-8 cells. The experiments were conducted using the methods described in Example 1.

Results

Figure 2A:
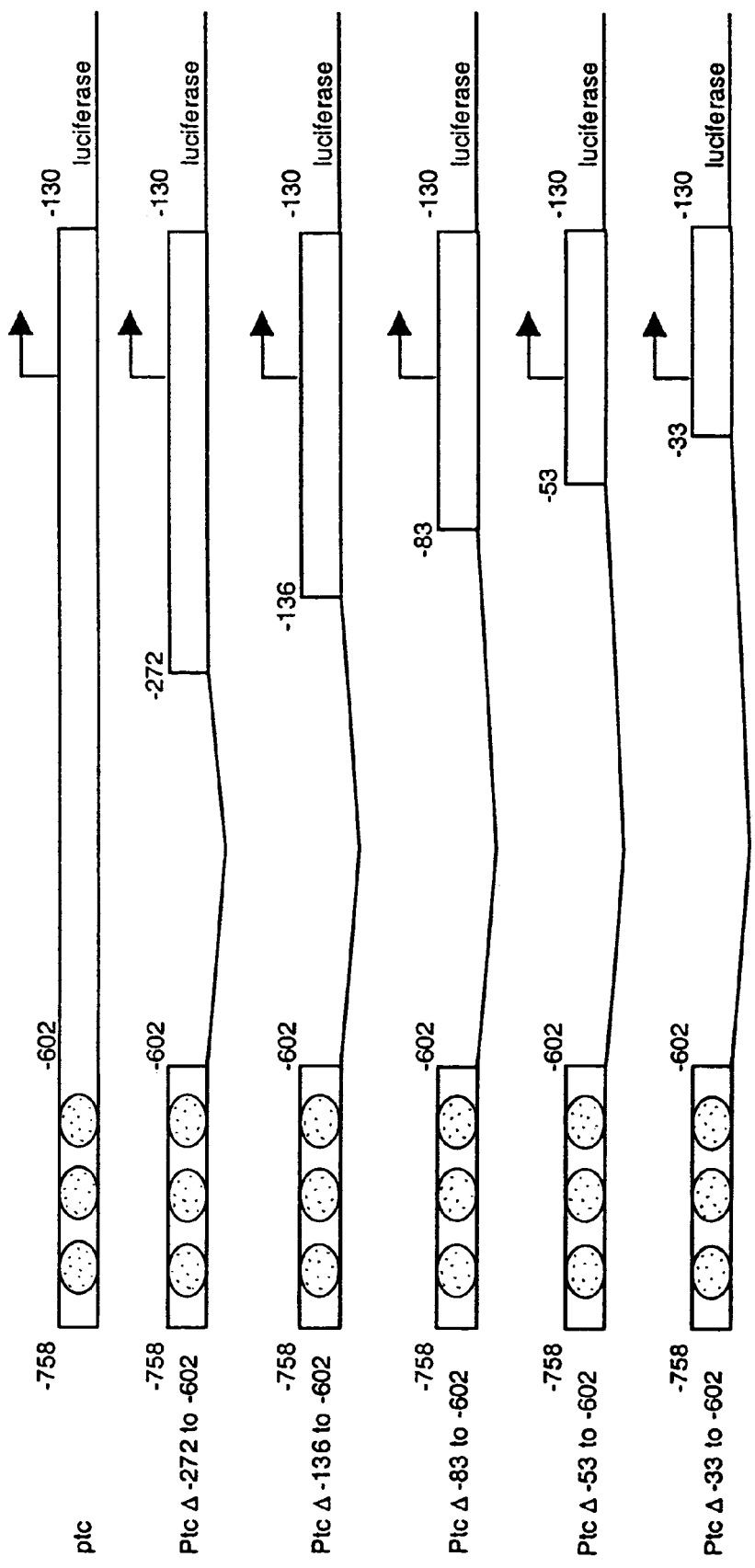
FIG. 2A is a schematic diagram of the ptc promoter region.
Figure 2B:
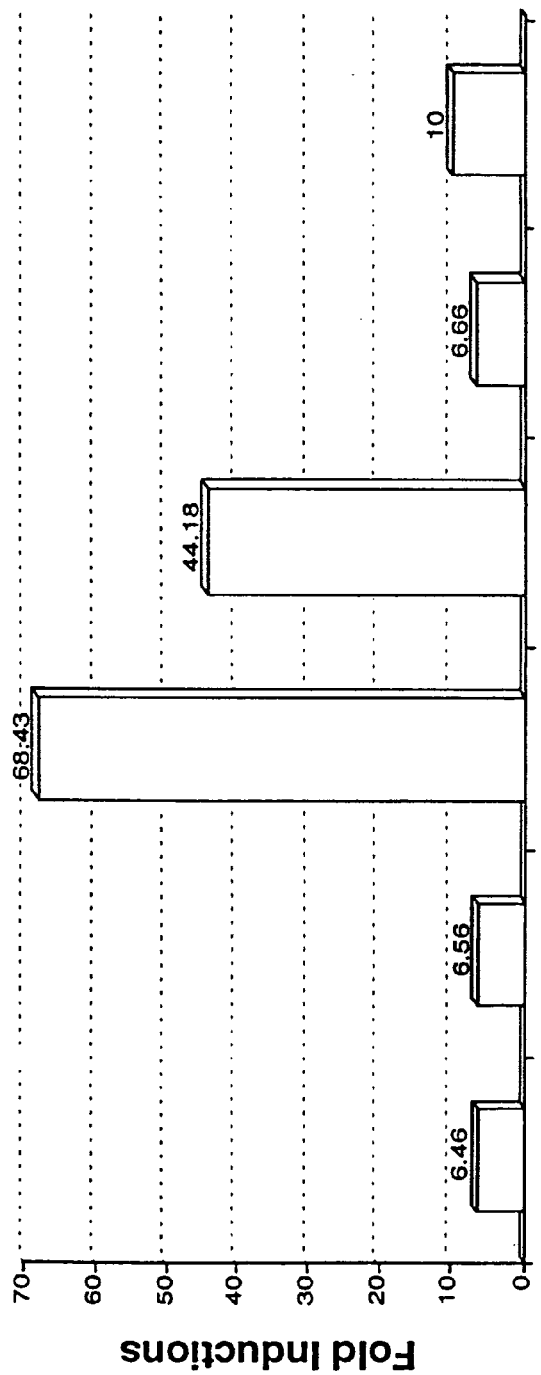
FIG. 2B is a plot of the induction of the luciferase reporter using various ptc promoter truncations.

The luciferase activity was induced about 6 fold when treated with HH-N conditioned medium compared to treatment with the S2 conditioned medium (FIG. 2B). Higher folds of induction were achieved when various regions of the ptc promoter were deleted (FIGS. 2A and 2B). The luciferase reporter activity was most sensitive to HH signaling, giving about 60 to 70 folds induction, when regions between −136 to −602 were deleted.

The consensus binding sequence of Gli, the vertebrate homolog of Ci, was found in the promoter region of the ptc.

Figure 2C:
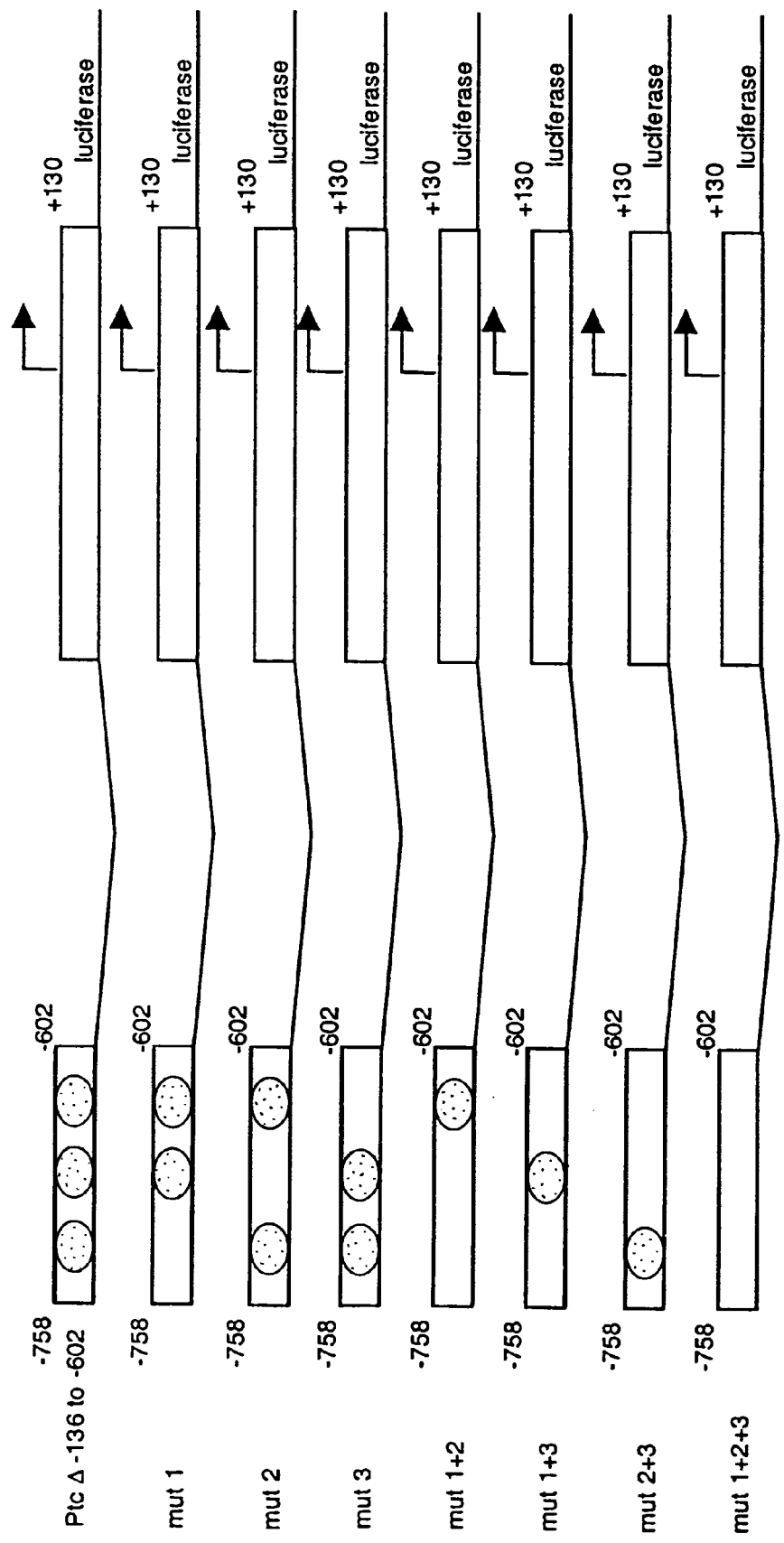
FIG. 2C is a schematic showing the Ci binding site mutations.
Figure 2D:
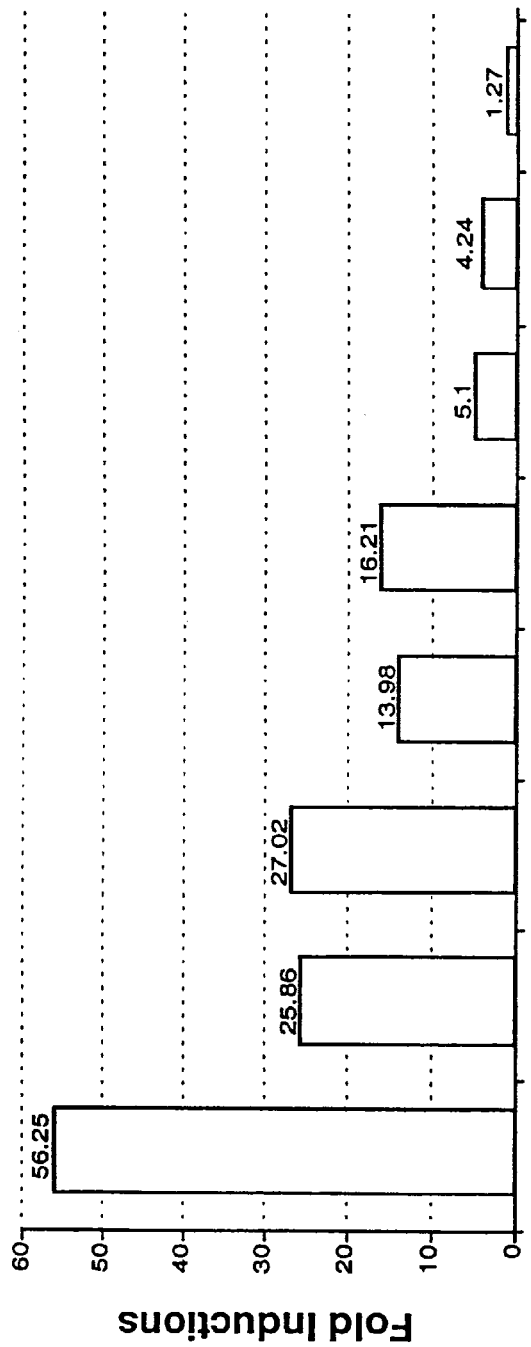
FIG. 2D shows the results from mutagenesis of the Ci binding sites in the ptc promoter.

The role of Ci in activating ptc transcription through these consensus sequences was examined. The three potential Ci binding sites in the ptc promoter of the reporter construct were mutagenized in order to examine the role of Ci in the activation of the luciferase reporter (FIG. 2C). Mutagenizing one binding site reduced the reporter activity to one half to one quarter, whereas mutagenizing all 3 potential binding sites completely abolished the reporter activity (FIG. 2D). The significant decrease in the reporter activity when potential Ci binding sites were mutagenized implicated that the activation of the reporter was mediated specifically by Ci through the ptc promoter. Since ptc expression required Ci, the ptc induction by HH must be slower than the Ci induction, as was seen in FIGS. 1A and 1B.

Example 3

Role of Phosphatase in HH-Signaling Pathway

Methods

Immunoprecipitation and Treatment with Phosphatase cl-8 cells were incubated in conditioned medium for 4 hours and lysed on ice for 20 minutes in 1 ml of NP-40 lysis buffer per T75 flask. The lysate was incubated with 100 µl of anti-Ci 2A1 or 0.3 µl of normal rat serum at 4° C. for 2 hours. 50 µL of 50% Protein G beads were added and incubated for 1 hour. The beads were collected and washed in NP-40 lysis buffer, then in lambda phosphatase buffer (50 mM Tris pH 7.8, 5 mM dithiothritol, 20 mM $MnCl_2$, 100 mg/ml bovine serum albumin, 20 µg/ml aprotinin, 20 µg/ml leupeptin, 1 µg/ml pepstatin A, 2.5 µg/ml antipain, 100 µM PMSF). The beads were resuspended in 50 µl of lambda phosphatase buffer, plus 1 mM of sodium orthovanadate or 1.5 µl (30 unit) of lambda phosphatase according to the procedure. Each sample was incubated at 30° C. for 1 hour, then washed in NP-40 lysis buffer, and was boiled in SDS sample buffer for analysis.

Phosphatase Inhibitors

Tautomycin (TAU) and okadaic acid (OA) were purchased from Calbiochem and dissolved in dimethyl sulfoxide (DMSO) to different concentrations. The phosphatase inhibitors were mixed with conditioned medium and the concentration of DMSO was adjusted to 0.2% for each sample. cl-8 cells were incubated with conditioned medium and phosphatase inhibitor mixture for 4 hours and lysed for analysis.

Results

Figure 3A:
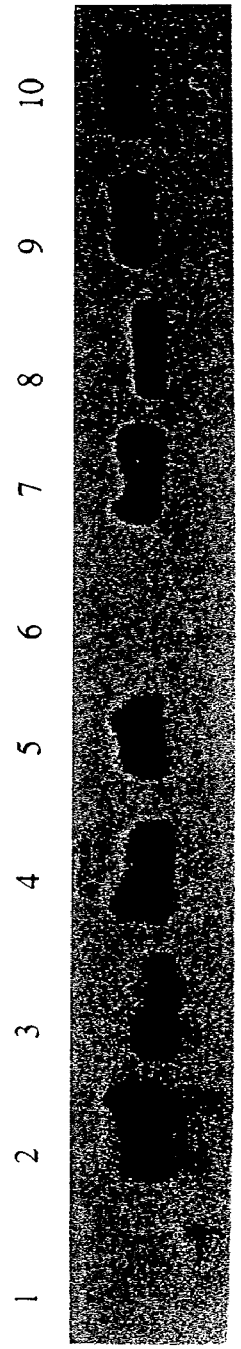
FIGS. 3A and 3B show the role of phosphatases and phosphatase inhibitors in HH signaling pathways. (Tautomycin=TAU; Okadaic Acid=OA)

Cell lysate from cl-8 cells treated with or without HH-N conditioned medium was immunoprecipitated and incubated with lambda phosphatase, a general phosphatase capable of releasing phosphate group from serine, threonine, and tyrosine. Treatment with lambda phosphatase shifted the low mobility form of Ci to the high mobility form (FIG. 3A). The effect of lambda phosphatase was reversed by sodium orthovanadate (FIG. 3A), a known inhibitor for lambda phosphatase, indicating that the mobility shift was indeed caused by dephosphorylation, but not other nonspecific modification or proteolysis. Therefore, the different mobility forms of Ci were due to different phosphorylation status of the protein—the high mobility form of Ci being less phosphorylated and the low mobility form being more phosphorylated.

Isoelectric-focusing electrophoresis followed by SDS-polyacrylamide gel electrophoresis (the 2-D gel) showed that the isoelectric point of Ci shifted towards more basic pH when immunoprecipitated from cl-8 cells treated with HH-N conditioned medium (data not shown), consistent with the observation that Ci was less phosphorylated upon HH signaling. When Ci isolated from HH stimulated cl-8 cells was treated with phosphatase, the isoelectric point of Ci shifted to even more basic pH, suggesting that Ci was not completely dephosphorylated upon HH signaling, but just less phosphorylated.

Figure 3B:
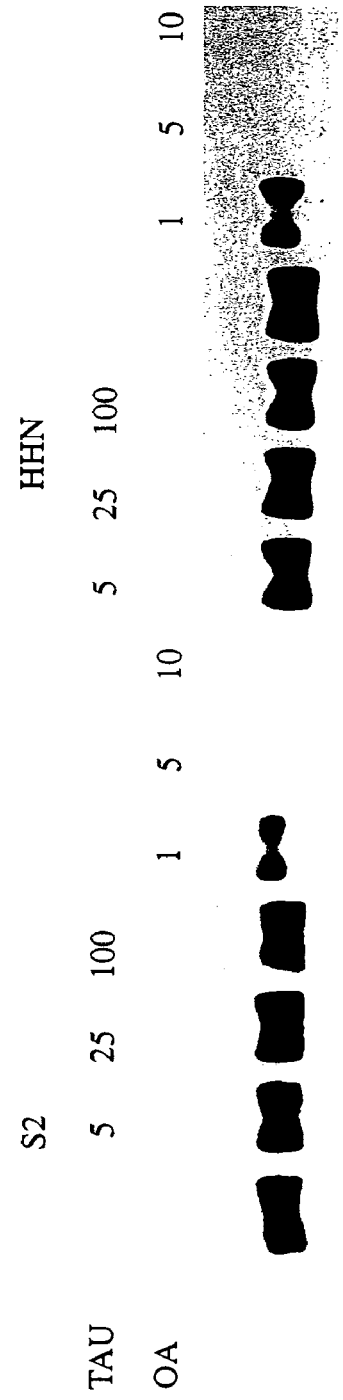

The reduced phosphorylation of Ci by HH signaling suggested that a phosphatase may be involved in the signaling. The possibility of the involvement of a phosphatase in the pathway was investigated by looking at the effect of TAU and OA on Ci induction in cl-8 cells. TAU and OA are both inhibitors of serine/threonine protein phosphatases, with distinctive potency towards different phosphatases. TAU is a potent phosphatase 1 (PP1) inhibitor ($IC_{50}$=10 nM). TAU, up to 100 nM, did not to have any effect on Ci, regardless of the presence of HH or not (FIG. 3B). In contrast, in the absence of HH signaling, 1 nM of OA significantly reduced the Ci level and shifted Ci to the low mobility form, which was due to the increased phosphorylation of Ci (FIG. 3B). With 5 to 10 nM of OA, Ci was completely undetectable. OA not only reduced the endogenous Ci level in the absence of HH, but also overcame the induction effect of HH to reduce the Ci level and mobility in the presence of HH. The ability of OA, a potent phosphatase 2A inhibitor, to inhibit the effect of HH on Ci, together with the fact that Ci was less phosphorylated upon HH signaling, suggested that a phosphatase was required for the HH signaling.

Example 4

Shh-Polypeptide Mediated Signaling in Chick Embryo Neurotube Explants

Most of the components identified so far in the HH signaling pathway are conserved from Drosophila to vertebrates. The phosphatase activity found in cl-8 cells may also be conserved in vertebrates. Sonic HH(SHH), the vertebrate homolog of HH, induced the floor plate marker hepatocyte nuclear factor 3β (HNF3β) and motor neuron marker islet-1 (Isl-1) in the developing neurotube. In chick embryo neurotube explant, exogenously provided SHH induced the expression of HNF3β and Isl-1. 1 nM of OA reduced the induction of HNF3β and Isl-1 by 2.5 mg/ml of SHH, but the effect was reversed by 10 mg/ml of SHH. 10 nM of OA completely blocked the induction of HNF3β and Isl-1 even in the presence of 10 mg/ml of SHH. The results indicated that regulation of the HH signaling by phosphatase may be a conserved and important mechanism.

Example 5

Cellular Localization of the Ci Polypeptide

Nuclear and Cytoplasmic Fractionation of cl-8 Cells cl-8 cells incubated with conditioned medium for 4 hours were harvested, and resuspended in buffer (15 mM Hepes, $K^+$, pH 7.6, 10 mM KCl, 5 mM $MgCl_2$, 0.1 mM EDTA, 0.5 mM EGTA, 350 mM sucrose, 1 mM 2-mercaptoethanol, 1 mM $Na_2S_2O_5$ protease inhibitors, 5 mM NaF, 5 mM $Na_2P_4O_7$). The suspension was homogenized with Dounce pestle B, and centrifuged at 8,000×g for 15 minutes at 4° C. The supernatant was saved as the cytoplasmic fraction and the pellet was resuspended in buffer AB (15 mM Hepes, $K^+$, pH 7.6, 110 mM KCl, 5 mM $MgCl_2$, 0.1 mM EDTA, 2.5 mM 2-mercaptoethanol, 1.25 mM $Na_2S_2O_5$ protease inhibitors, 5 mM NaF, 5 mM $Na_2P_4O_7$), and centrifuged at 2,000×g for 10 minutes at 4° C. over 0.8 M sucrose cushion in buffer AB. The pellet was washed and resuspended in buffer AB. The protein was precipitated by 0.4 M $(NH_4)_2SO_4$ for 30 minutes at 4° C., then centrifuged at 55,000×g for 30 minutes at 4° C. The supernatant was saved as the nuclear fraction. Other methods that were used are described in Example 1.

Figure 4:
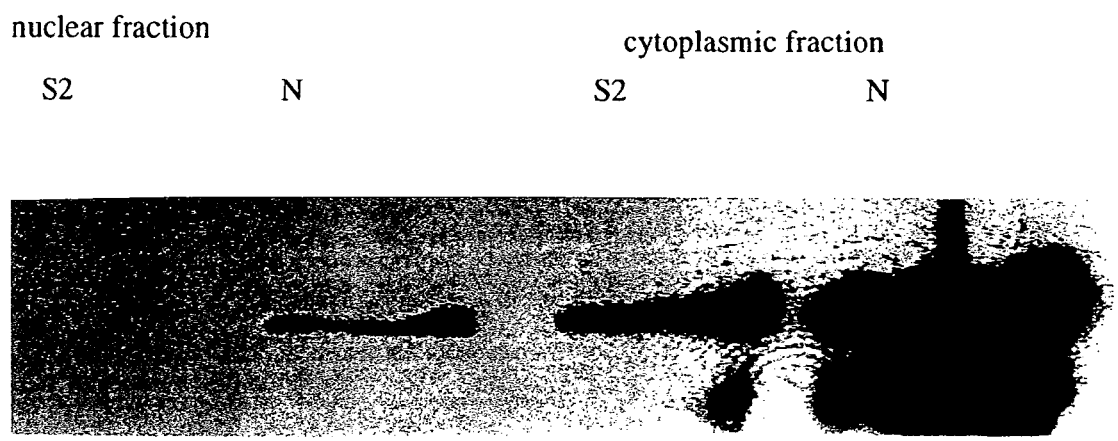
FIG. 4 shows the occurrence of Ci in the nucleus and cytoplasm in the presence and absence of the HH signaling.

Results cl-8 cells either treated or untreated with the HH-N conditioned medium were collected. The cells were fractionated into the nuclear fraction and the cytoplasmic fraction. Consistent with the previous observation, Ci was found mainly in the cytoplasmic fraction and barely in the nuclear fraction in the absence of HH (FIG. 4). However, the amount of Ci in the nucleus increased significantly upon HH signaling (FIG. 4). A carboxy-terminal domain of Ci was recently identified as sufficient and necessary for the tethering of Ci in the cytoplasm. The observed nuclear localization of Ci upon HH signaling suggested that the HH signal may relieve the anchorage of Ci in the cytoplasm and allow it to enter the nucleus.

Example 6

Induction of COUP-TFII mRNA by Shh-N Polypeptide

Methods

Cell Culture System and Shh-N Source

The P19 mouse embryocarcinoma cell line which was earlier shown to contain increased levels of COUP-TF transcripts after retinoid treatment was utilized. Jonk, L. J. C., et al., *Mechan. of Dev.* (1994) 47:81–97). Conditioned media obtained from COS-1 cells transfected with mouse Shh-N cDNA expression plasmid or purified *E. coli* expressed recombinant Shh-N was used.

RNase Protection Assay

Briefly, a total of 20 μg RNA was hybridized to a 450 (FIG. 5A) or 120 (FIG. 7B) nucleotide riboprobe that corresponds to the 5' untranslated region (UTR) of the COUP-TFII gene along with a 670 (FIG. 5A) or 102 (FIG. 7B) nucleotide riboprobe of the murine Cyclophilin A coding region. The RPA II™ kit from Ambion was used to perform the RNase protection assay. The products were subjected to RNase digestion and analyzed on a 6% urea polyacrylamide gel.

Results

P19 cells were treated with 0.2 (FIG. 5A, lane 2), 0.5 (FIG. 5A, lane 3), and 1 nM (FIG. 5A, lane 4) of Shh-N for 24 hours and cells were harvested and total RNA was obtained. An RNase protection assay was performed as described above. Undigested probe was run in lane 5.

Figure 5A:
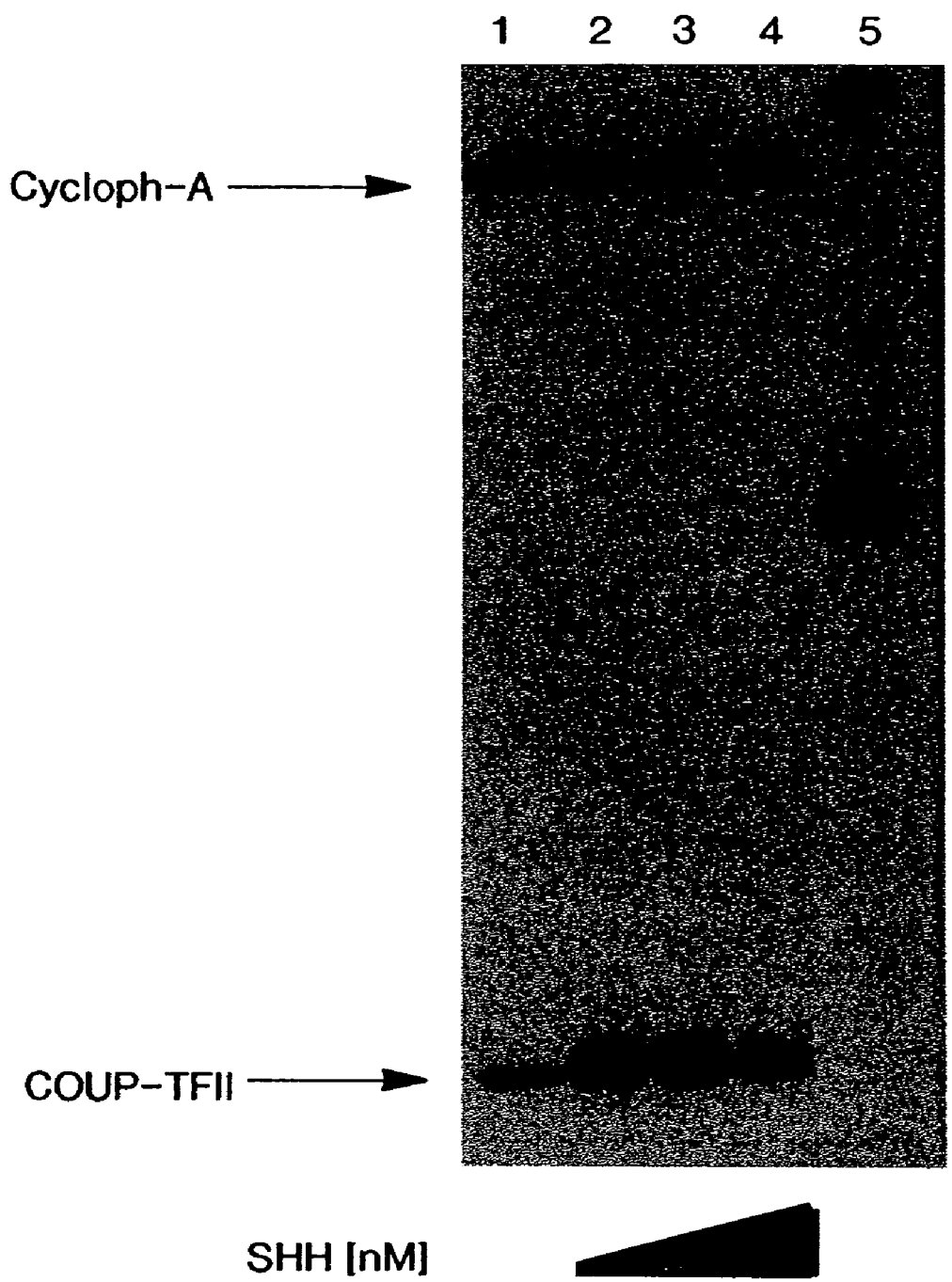
FIG. 5A shows the induction of COUP-TFII mRNA by Shh-N polypeptide.

Conditioned media obtained from either COS-1 cells transfected with mouse Shh-N cDNA expression plasmid (data not shown) or from purified *E. coli* expressed recombinant Shh-N induced COUP-TFII expression in the P19 cells. Densitometric analysis revealed a significant increase in COUP-TFII mRNA and this increase was observed at concentrations as low as 0.2 nM Shh-N, (FIG. 5A, lane 2). This concentration of Shh-N required for induction of COUP-TFII expression was similar to the low levels that was required for regulating other Shh-N target genes and for binding to its putative receptor, patched (ptc). Roelink, H. et al. *Cell*, 81:445–455, 1995; Monsoro-Burq, A. H. et al. *Mech. of Dev.*, 53:157–170, 1995; Stone, D. M., et al. *Nature* 384:129–134, 1996; Marigo, V. et al. *Nature* 384:176–179, 1996.

Example 7

Identification of Sonic Hedgehog Response Element

Methods described above in Example 6 were used in addition to the following protocols. P19 cells were transfected with a ShhRE-tkLUC reporter plasmid and three copies of a mutant element called mShhRE-tkLUC and treated with or without 1 nM Shh. Cell lysates were obtained after 30 hours and were later assayed for luciferase reporter activity. A graph (FIG. 5B) representing relative luciferase units per twenty µg (RLU/20 µg) was plotted using results obtained from three separate experiments (mean±sd).

Results

In order to identify the target element(s) for Shh-N signaling, a 1.6 kb promoter fragment of COUP-TFII (−1455 to +117) was placed upstream of a CAT reporter gene and was initially used in a transient transfection assay where it was significantly upregulated by 1 nM Shh-N (data not shown). Extensive analysis of 5' deletions identified a region between −1343 and −1070 that harbors most of this Shh-responsive activity.

Figure 5B:
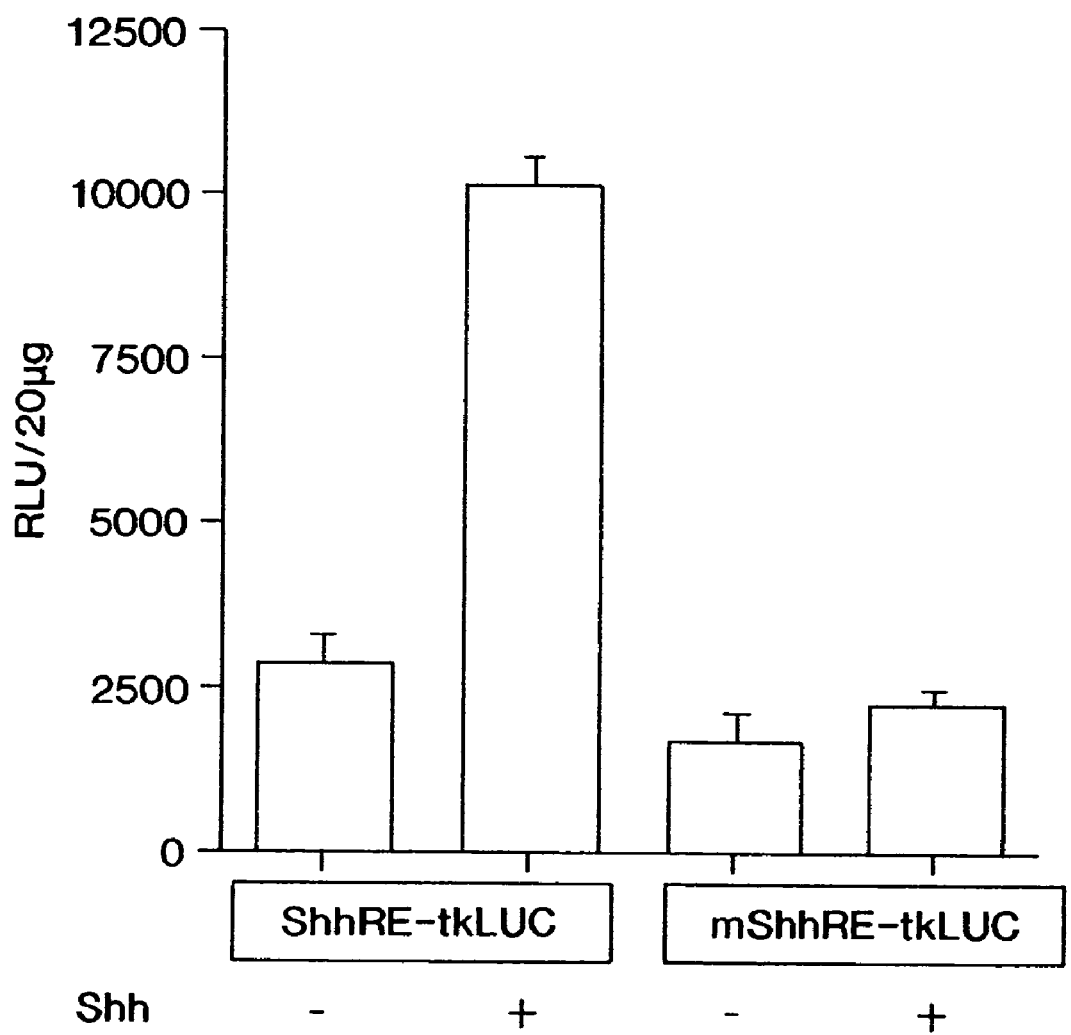
FIG. 5B shows the induction of luciferase activity with the ShhRE-tkLUC reporter plasmid and the mShhRE tkluc reporter plasmid.

A specific sequence within this region (between −1316 and −1298) was subsequently shown to activate luciferase reporter activity when cloned upstream of a heterologous HSV thymidine kinase (tk) promoter (FIG. 5B). Most importantly, point mutations introduced within this element (—GTTCTACATAATGCGCCG—; wt to —GTTCTACgTgATGCGCCG—; mut.) (SEQ ID NOS:1 and 3, respectively) completely abolished this activation by Shh-N (FIG. 5B). Therefore, this region was defined as a Sonic hedgehog response element (ShhRE).

Example 8

ShhRE is Different from GliRE

Methods described in Example 6 were used in addition to the following protocols. P19 cells were treated with or without Shh-N for 24 hours and nuclear extracts were obtained and used in an electrophoretic mobility shift assay (EMSA) with radiolabeled ShhRE. The following oligos were used as competitors or probes in these assays; WT ShhRE—GTTCTACATAATGCGCCG—; mShhRE—GTTCTACgTgATGCGCCG—; GliRE—TCCCGAAGACCACCCACAATGA—. (SEQ ID NOS:1, 3, and 4, respectively) Different amounts of unlabeled Gli response element (GliRE) (FIG. 5C, lane 3, 100×; lane 4, 50×; lane 5, 25×; and lane 6, 10×) or ShhRE (lane 7; 100×, lane 8; 50× and lane 9; 10×) was used as a competitor at the indicated molar excess.

In EMSA, radiolabeled probe was incubated with the nuclear extracts (10 µg) along with 4 µg poly dG-dC in a binding reaction containing 10 mM Tris pH 7.5, 50 mM NaCl, 1 mM EDTA, 1 mM DTT, 0.1 mg/ml BSA, and 5% glycerol. Later the mixture was loaded onto a 5% polyacrylamide gel and the retarded complexes were separated in 1×TBE buffer and analyzed using autoradiography.

Results

Figure 5C:
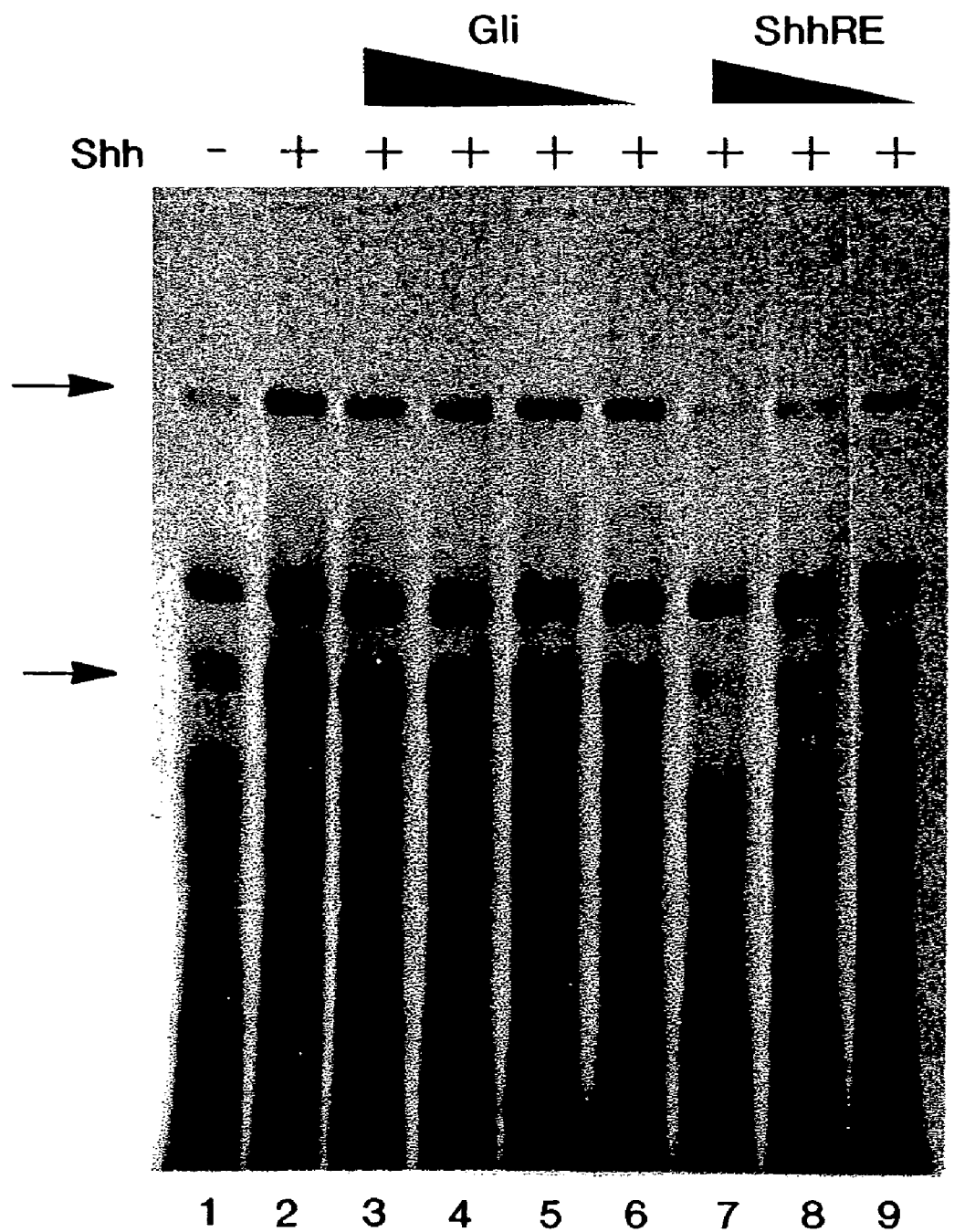
FIG. 5C shows that ShhRE is distinct from GliRE.
Figure 7A:
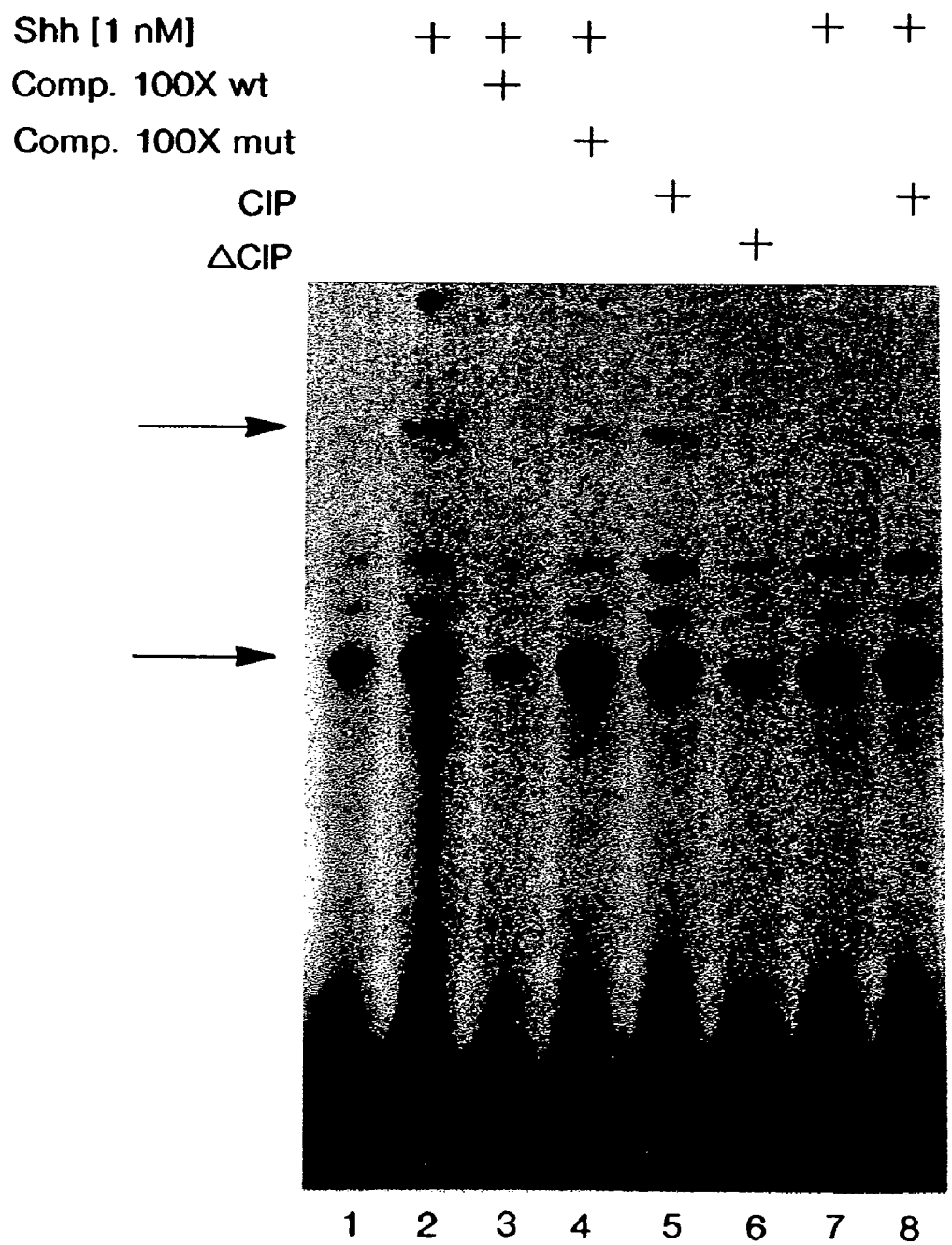
FIG. 7A shows an EMSA.

As shown in FIG. 5C, the binding of two specific complexes were enriched in response to Shh-N treatment (lanes 1 & 2). This binding was specific, since it can be competed by ShhRE (FIG. 5C, lanes 7–9), but not by a mutated ShhRE (FIG. 7A, lanes 1–4). Hence, Shh-N enhances the binding of a putative transcription factor(s) to the ShhRE on the COUP-TFII promoter. Recent reports have identified a response element on HH-induced target promoters that are bound by Ci/Gli family of transcription factors. However, the ShhRE in the COUP-TFII promoter does not resemble a GliRE. EMSA's performed using unlabeled GliRE as a competitor, clearly indicate that the GliRE was unable to compete for binding to the ShhRE in the COUP-TFII promoter (FIG. 5C, lanes 3 through 6). Hence the factor that binds to the ShhRE is distinct from GliRE. The ShhRE includes an AT rich motif followed by a GC core and both of them are important for Shh-mediated activity.

Example 9

ShhRE-Mediated Activity is a Direct Result of Shh-N Signaling

Methods described in Example 6 were used in addition to the following protocols. P19 cells were co-transfected with either three copies of the ShhRE or mutant ShhRE (mShhRE) element placed upstream of the tk-CAT along with tk-LUC plasmid as an internal control. Cells were treated with 1.0 nM Shh-N (12 hours) and with or without 50 µM cycloheximide (Chx) for 14 hours and harvested to obtain total RNA. Sixty µg of total RNA from these cells were used in an RNase protection assay. RNase protection assays were performed as described in Example 6. Specific riboprobes were generated to analyze the relative levels of the CAT and LUC mRNA levels. A 255 bp region of the CAT coding sequence or 123 bp of the luciferase coding region was used to generate an antisense riboprobe and was hybridized with 60 µg of total RNA, obtained from transfected P19 cells. The amount (50 µM) and extent (14 hours) of cycloheximide treatment was based on inhibition of protein synthesis as indicated by a significant loss in reporter enzyme activity.

Results

Figure 6:
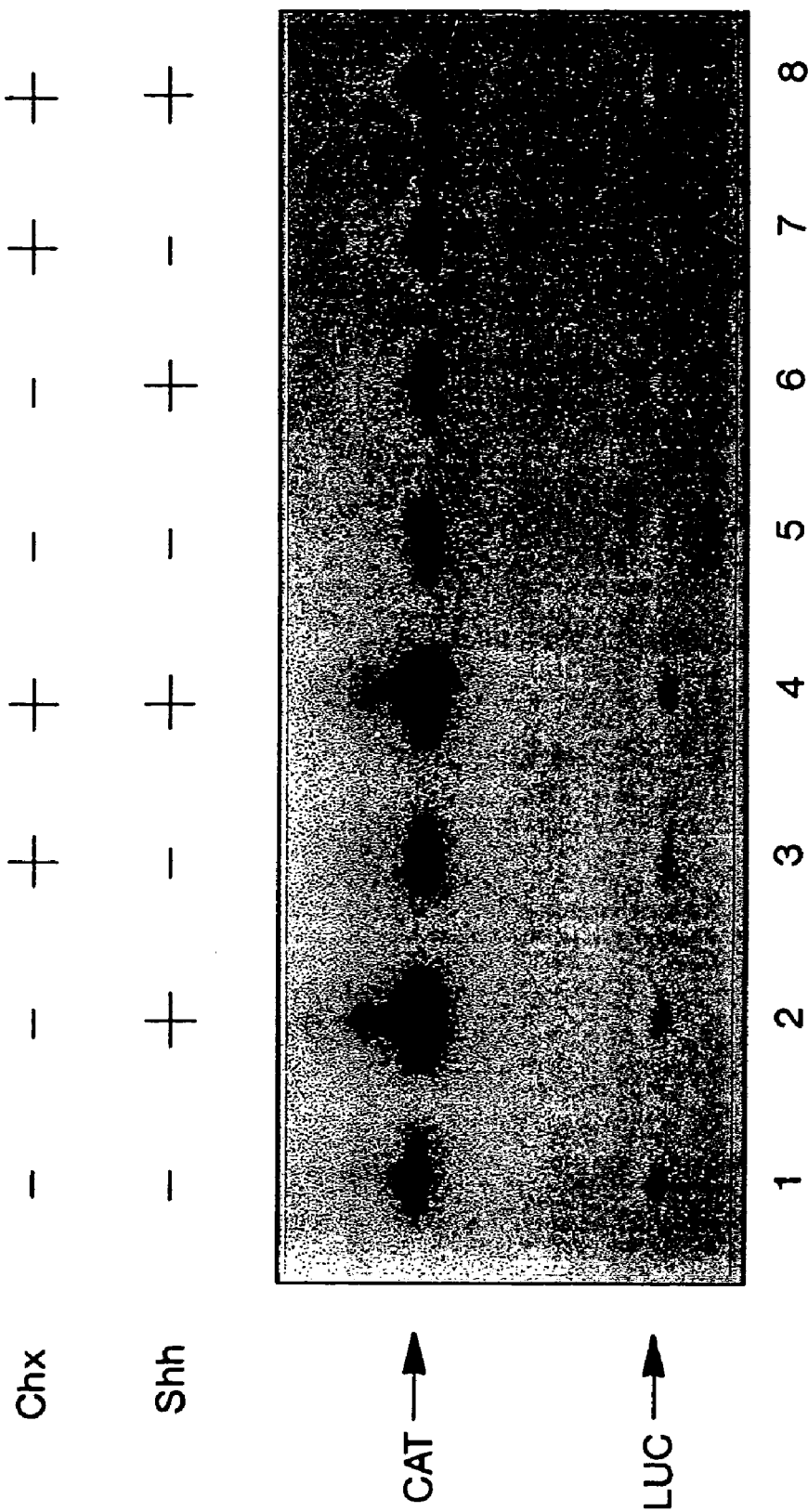
FIG. 6 shows that ShhRE-mediated activity is a direct result of Shh-N signaling.

Cells were transfected with the ShhRE-tkCAT plasmid (FIG. 6, lanes 1 through 4) or mutant ShhRE-tkCAT plasmid (FIG. 6, lanes 5 through 8) and treated with 1 nM Shh-N in the presence and absence of 50 µM cycloheximide. A plasmid encoding the luciferase reporter gene driven by a minimal tk promoter was co-transfected as an internal control. The Shh-induced increase in CAT mRNA was not altered by the presence of cycloheximide (FIG. 6, lanes 2 and 4). In contrast, CAT and luciferase activities are both inhibited in the presence of cycloheximide. This result suggested that the factor(s) that binds and activates the ShhRE was a primary target of the Shh-N signal pathway and its activation does not require protein synthesis.

Example 10

Role of Phosphatase in Shh-N Mediated Activation of COUP-TFII

Methods described in Example 6 and Example 8 were used in addition to the following protocols. P19 cells were treated with 1 nM Shh-N (FIG. 7A, lane 2) and nuclear extracts were obtained and used in an EMSA with radiolabeled oligonucleotides that correspond to the ShhRE. Cells were harvested after 24 hours of treatment and the nuclear extract was obtained for the binding reactions. Calf-Intestinal phosphatase was added to the untreated extracts (20 units for 15 minutes at room temperature) prior to binding reactions and the protein concentration was adjusted with carrier bovine serum albumin (BSA). Later these samples were subjected to an EMSA as described above. Unlabeled oligonucleotides (FIG. 7A wt, lane 3; mutant, lane 4) were used in 100-fold molar excess to study the specific complexes that were induced after Shh-N treatment.

Figure 7B:
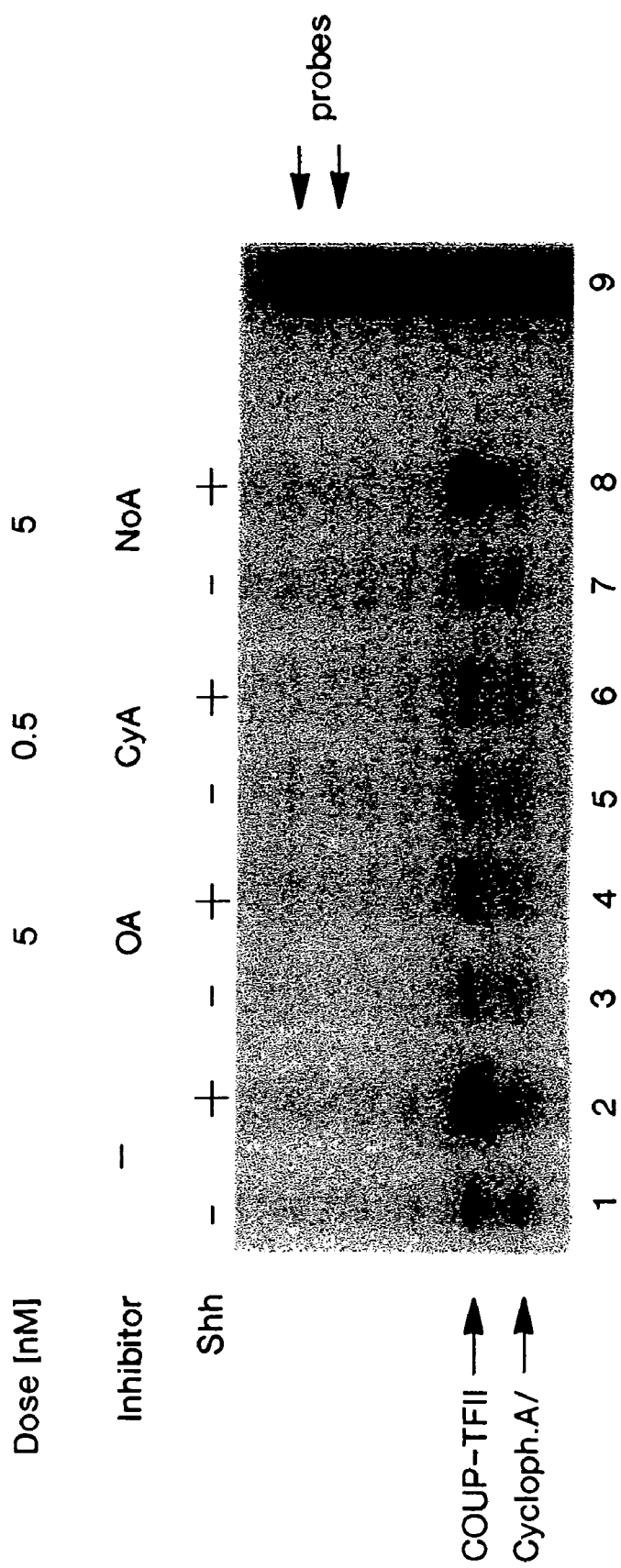
FIG. 7B shows endogenous levels of COUP-TFII mRNA after treatment with phosphatase inhibitors.
Figure 7C:
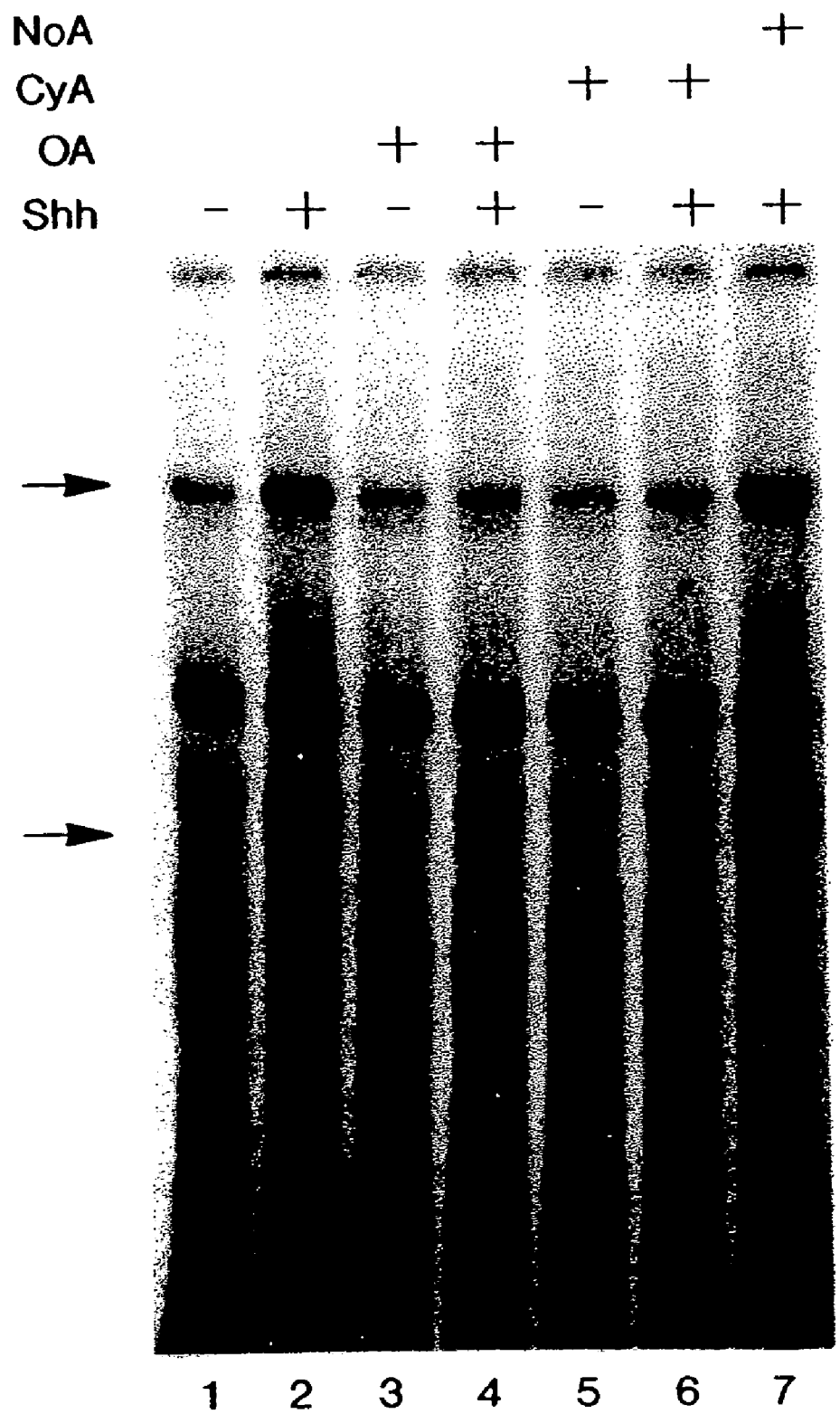
FIG. 7C shows an EMSA.

P-19 cells were treated with phosphatase inhibitors to study the endogenous levels of COUP-TFII mRNA. Total RNA was obtained after co-treatment with 5 nM OA (FIG. 7B, lane 3 and 4), 0.5 nM calyculin A (CyA) (FIG. 7B, lanes 5 and 6) or 5 nM of the inactive congener Nor-Okadone (NoA) (FIG. 7B, lane 9) for 12 hours, along with or without 1.0 nM Shh-N (FIG. 7B, lanes 2, 4, 6, 8, and 9) for 24 hours. Total RNA was isolated from these cells and 20 μg of RNA was used in a RNase protection assay as described above in Example 6. A region of the murine Cyclophilin A cDNA was used to generate riboprobe and was used as an internal control. P19 cells were co-treated with (FIG. 7C, lane 2, 4, 6, and 7) or without (FIG. 7C, lane 1, 3, and 5) 1.0 nM Shh-N and 5 nM OA (lane 3 and 4), 0.5 nM CyA (FIG. 7C, lane 5 & 6) or 5 run NoA (FIG. 7C, lane 9). Cells were harvested after 24 hours of treatment and the nuclear extract was obtained for the binding reactions. Extracts were subjected to an EMSA as described earlier.

P19 cells were treated with or without 1 nM Shh for 36 hours and nuclear extracts from these cells were obtained as described earlier. A protein phosphatase assay system™ (Life Technologies, Bethesda) was used to quantitate the phosphatase activity present in the control and induced extracts. P19 cells were treated with or without 1 nM Shh for 36 hours and nuclear extracts from these cells were obtained and incubated with 2 nM OA or 4 nM Inh-2 protein for 15 minutes at 30° C. Results are expressed as mean±sd from three separate experiments.

P19 cells were cotransfected with the ShhRE-SV40LUC plasmid (3×ShhRE-SV40LUC) and an expression plasmid for PP1 (RSV-PP1), PP2A (CMV-PP2A), PPIV (CMV-PPIV), and PPV (CMV-PPV). In addition an empty pBKRSV or pCMV5 vector was also cotransfected in the control wells. Cells were treated with and without 1 nM Shh and harvested after 36 hours. Cell lysates were obtained and 100 μg of this lysate was used to assay for reporter gene activity. A graph (FIG. 7E) representing relative luciferase units per 100 μg (RLU/100 μg) was plotted using results obtained from three separate experiments (mean±sd).

Results

To assess the role of phosphorylation in modulating Shh-inducible binding to the ShhRE, a non-specific calf-intestinal phosphatase (CIP) was incubated with both induced and uninduced nuclear extracts (FIG. 7A, lanes 5 through 8). Interestingly, although incubation of CIP with Shh-N treated extracts did not alter binding to radiolabeled ShhRE (compare lanes 7 and 8), CIP treatment of uninduced extracts was able to mimic the binding activity induced by Shh-N (compare lanes 1 and 5). Also, heat denatured CIP (ΔCIP) could not mimic this increased binding to ShhRE (lane 6). These observations suggested that the factor(s) that binds to this ShhRE was present in the nuclear extracts of untreated P19 cells and Shh-N treatment specifically alters its ability to bind DNA by dephosphorylation.

Phosphatase inhibitors such as OA and CyA were used to characterize the protein phosphatases that mediate the dephosphorylation. OA is a potent inhibitor of serine/threonine specific protein phosphatases such as PP1, PP2A, PPIV, and PPV, but has no effect on PP2B and PP2C. Five nM OA or 0.5 nM CyA, when treated along with Shh-N (FIG. 7B, lanes 3 through 6) resulted in complete inhibition of the induced COUP-TFII mRNA. In contrast, 5 nM of the NoA was incapable of inhibiting the Shh-induced levels of COUP-TFII transcripts (FIG. 7B, lane 7 and 8).

The effect of these inhibitors of phosphatase activity on Shh-induced protein binding to an ShhRE (FIG. 7C) was tested. 5 nM OA (FIG. 7C, lanes 3 and 4) or 0.5 nM CyA (FIG. 7C, lanes 5 and 6) treatment, abolished the Shh-induced binding to radiolabeled ShhRE. However, the inactive congener, NoA was unable to inhibit Shh-induced binding (FIG. 7C, lane 7).

In a separate experiment, the Shh-N mediated induction of ShhRE reporter gene activity was also shown to be completely blocked by 5 nM OA treatment (data not shown). Also, treatment of cells with 5 nM OA did not effect the ability of a constitutively active SV40 enhancer to drive the expression of the luciferase reporter gene activity (data not shown). These results provide conclusive evidence that OA and CyA specifically inhibit binding of a transcription factor to the ShhRE that results in lowered promoter activity and eventually leads to decreased COUP-TFII transcripts.

Figure 7D:
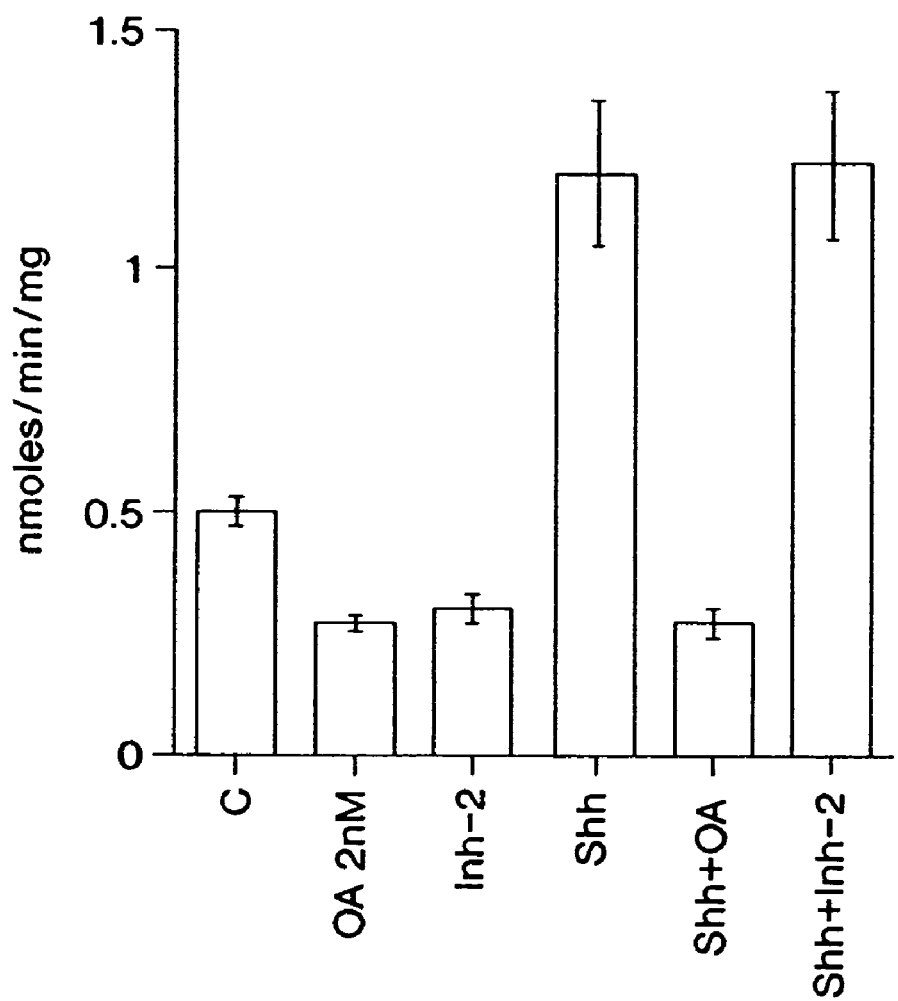
FIG. 7D shows phosphatase activity in Shh-induced p19 cells.

The direct involvement of the type of protein phosphatase in the Shh signaling pathway was assayed using a phosphatase assay system that quantitates the levels of PP1 and PP2A enzyme activity in the control and 1 nM Shh treated nuclear extracts in the absence or presence of 2 nM of Okadaic acid to ascertain the specific increase in the type of protein phosphatase. As shown in FIG. 7D, there is a net increase (2 fold) in phosphatase activity after Shh treatment which can be completely abolished with 2 nM OA treatment. In contrast, co-treatment with Inhibitor-2 (I"–2), a specific inhibitor of PP1, is unable to inhibit the Shh-induced phosphatase activity. This result further suggests that Shh treatment results in enhanced PP2A-like nuclear phosphatase activity which may contribute to increased COUP-TFII transcripts. Collectively, based on the results obtained form these experiments using phosphatase inhibitors and from the $IC_{50}$ values for these inhibitors, it is likely that a serine/threonine phosphatase such as PP2A, PPIV or PPV is involved in the Shh-N signaling pathway.

Figure 7E:
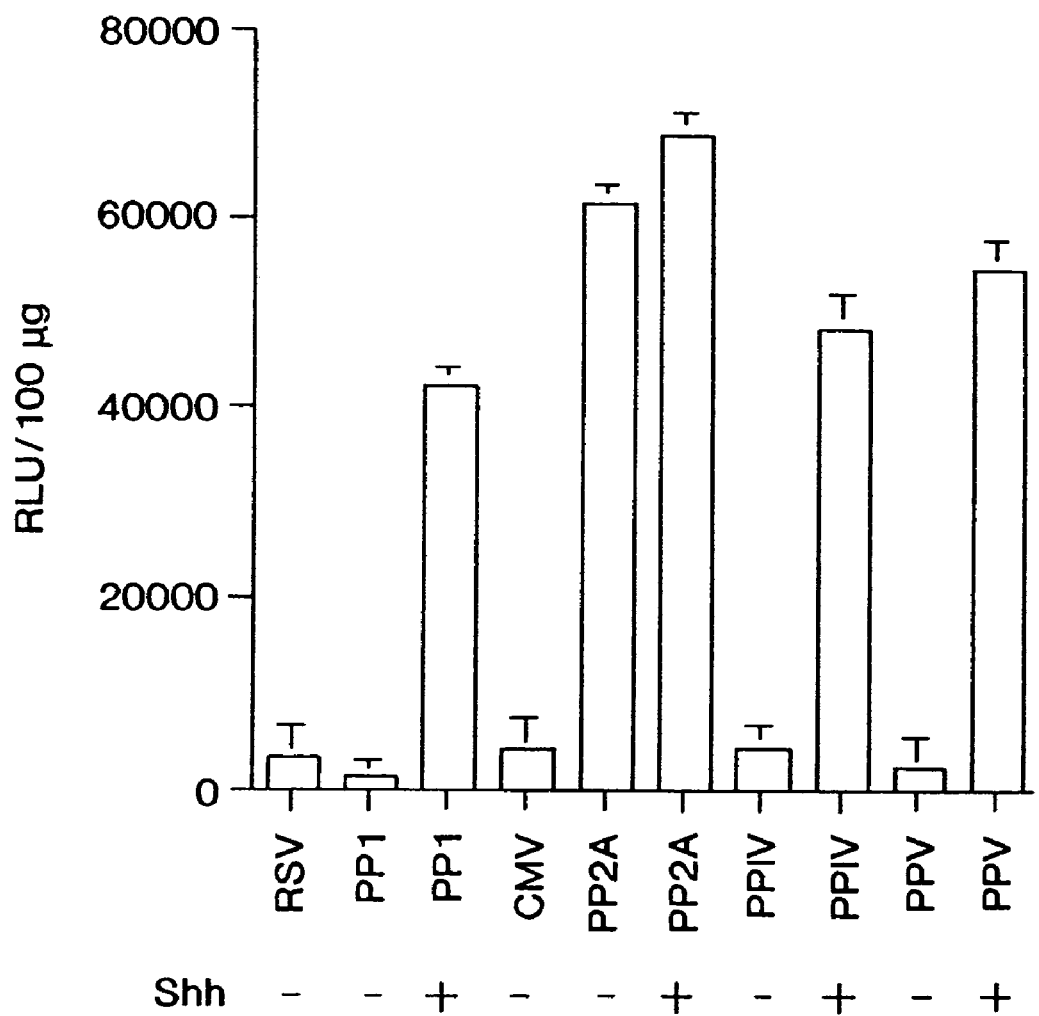
FIG. 7E is a graph representing luciferase levels in the presence of various phosphatase inhibitors.

The potential role of specific protein phosphatases in this pathway was further tested by transfecting P19 cells with the 3×ShhRE-SV40LUC plasmid along with expression plasmids that overexpress the catalytic subunit of PP1, PP2A, PPIV or PPV. Results from these experiments suggest that the catalytic subunit of PP2A, when overexpressed, can mimic the activity of Shh in untreated cells (FIG. 7E, compare CMV and PP2A). In contrast, neither PP1, PPIV or PPV could mimic this activity. In a separate experiment (data not shown), purified PP2A, when incubated with nuclear extracts obtained from untreated P19 cells, could stimulate binding to the ShhRE as detected in an EMSA. Collectively, these results suggested that a PP2A-like phosphatase can mediate this Shh-induced increase in target factor activity in vivo.

Example 11

Effect of Phosphatase Inhibitors on Isl1 Expression Induced by Shh-N

Methods described in Example 6 were used in addition to the following protocols. P19 cells were treated with (FIG. 8A, lanes 2 and 4) or without (FIG. 8A, lanes 1 and 3) 1 nM Shh-N for 24 hours and 5 nM OA (FIG. 8A, lanes 3 and 4) for 12 hours and total RNA was obtained. An internal control containing a 763 bp insert into the SphI site of the Islet-1 cDNA was transcribed in vitro to prepare sense-oriented RNA. 1 ng of this RNA along with 100 ng of total RNA from appropriately treated P19 cells was reverse transcribed using Superscript II™ and one-tenth of each reaction was PCR amplified. Specific primers for Islet-1; Forward primer: 5' TCA AAC CTA CTT TGG GGT CTT A 3' Reverse primer: 5' ATC GCC GGG GAT GAG CTG GCG GCT 3' and for COUP-TFII; Forward primer: 5' GAT ATG GCA ATG GTA GTC AGC ACG TGG 3'. Reverse primer: 5' AGC TTC TCC ACT TGC TCT TGG 3', SEQ ID NOS:5, 6, 7, and 8, respectively, were used to PCR amplify (94° C. for 1 minute, 54° C. for 1 minute, and 72° C. for 1 minute. Twenty-two cycles were used for amplifying Islet-1 and the resulting products were separated on a 1% agarose gel in TAE buffer and visualized by ethidium bromide staining. A 1 kb DNA ladder (Stratagene) was used to estimate the size of the products. A 427 bp Isl1 fragment and a 838 bp COUP-TFII fragment was used to estimate changes in mRNA levels.

Mouse embryos at embryonic day 9–9.5 were dissected in such a way as to remove surface ectoderm and somitic mesoderm and neural tubes were isolated from the level of rhombomere 8 in the rostral region to the first segmenting somite in the caudal region. Neural tubes were cultured for 24 hours, dorsal-side down on Millicell-CM membranes and overlayed with Matrigel™ containing 10 ng/ml NT-3, with L15 air in presence or absence of 5 nM OA. The explants were subjected to whole-mount immunostaining using a monoclonal antibody raised against mouse Islet-1 (39.4D5) or neurofilament (NFL) was used to analyze any changes in Islet-1 and NFL expression.

P19 cells were cotransfected with pBKCMV-Shh expression plasmid and a GliRE-CAT reporter plasmid (1 µg) as described earlier. Krishnan, V., et al., *Mol. Endo.*, 11:1458–1466, 1997. Cells cotransfected with pBKCMV-Shh or pBKCMV plasmid (200 ng) were treated with or without 5 nM OA for 14 hours and reporter gene activity was assayed as described earlier. Gorman, C. M., et al., *Mol. and Cell. Biology*, 2:1044–1051, 1982. Results are expressed as mean±sd from three separate experiments.

Results

Figure 8A:
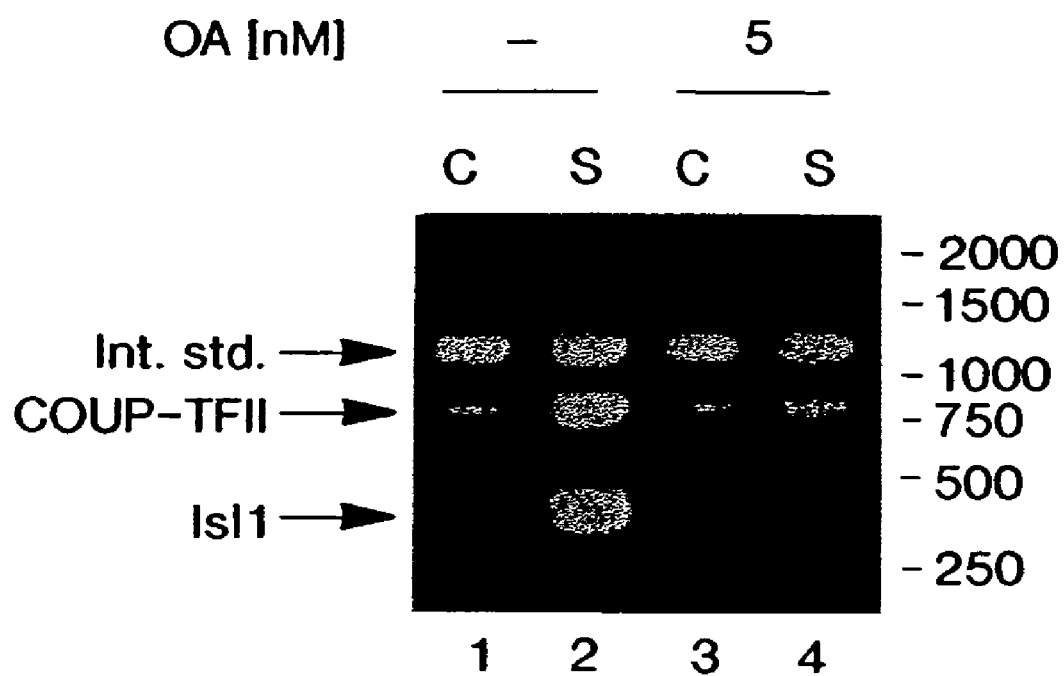
FIG. 8A shows the effect of phosphatase inhibitors on Isl1 expression and GliRE-mediated activity.
Figure 8B:
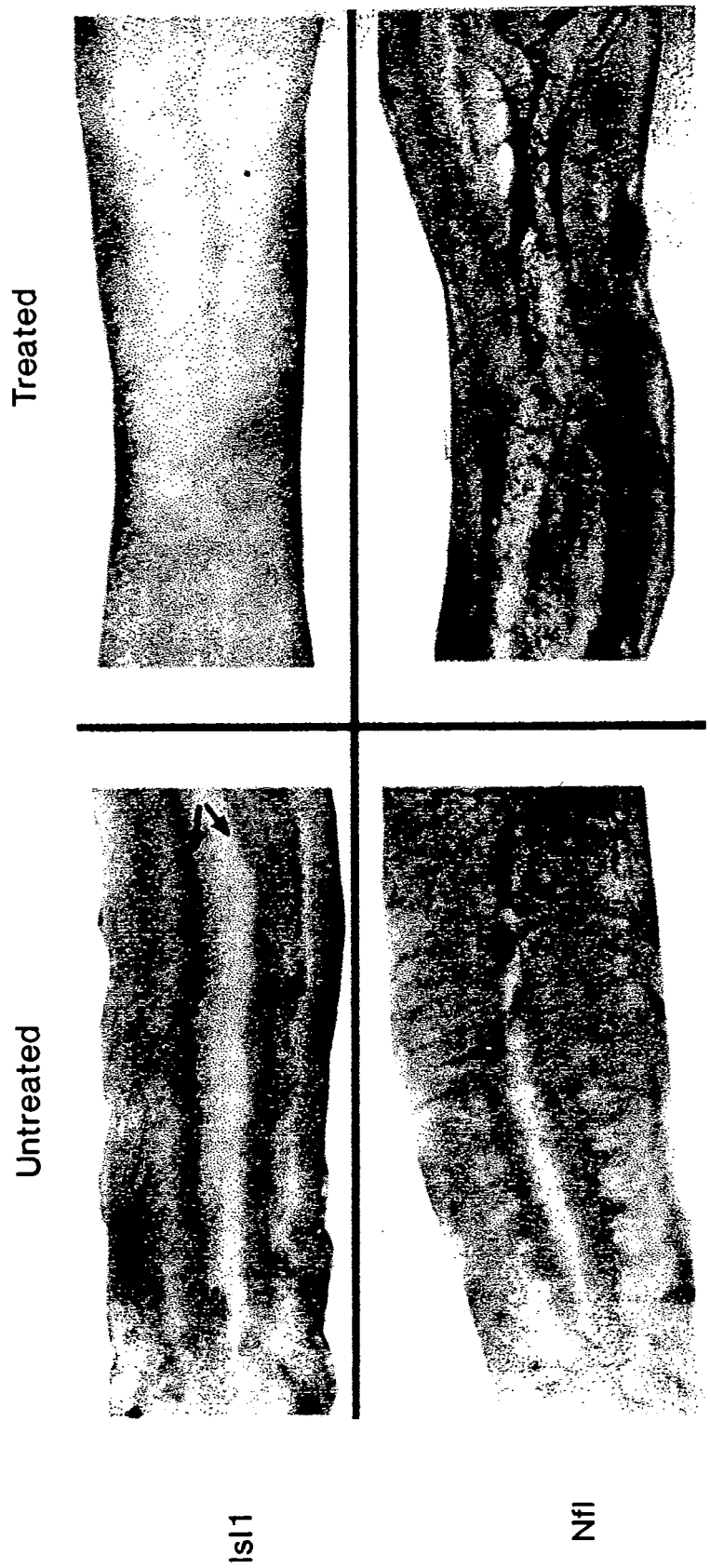
FIG. 8B is a photograph of neural tube explants with OA treatment.

In order to determine whether phosphatase mediated Shh signaling extends beyond COUP-TFII, Shh activation of Isl1 was analyzed in the presence of 5 nM OA. P19 cells treated with 1 nM Shh-N for 24 hours can induce Isl1 mRNA (FIG. 8A, lanes 1 and 2) and this induction was completely blocked by 5 nM OA treatment (FIG. 8A, lanes 3 and 4). Furthermore, 9.5 dpc mouse neural tube explants incubated with 5 nM OA for 24 hours, exhibit significantly decreased levels of immunodetectable Isl1 protein (FIG. 8B). However, this concentration of OA had no effect on the neurofilament staining within the neural tube.

Figure 8C:
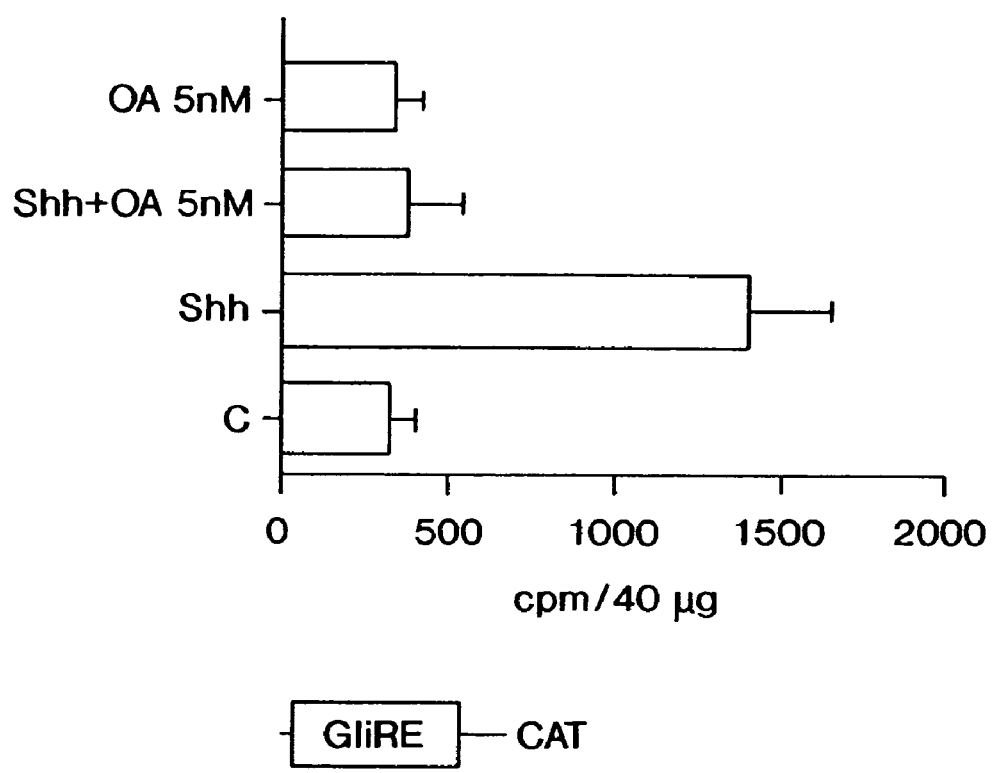
FIG. 8C is a graph showing Gli RE mediated activation by Shh and inhibition of OA.

The involvement of protein phosphatases in GliRE-mediated activation was verified using the GliRe in the HNF-3β 3'-enhancer as reported earlier. Sasaki, C. C., et al., *Development*, 124:1313–1322, 1997. As expected, in P19 cells, the GliRE-CAT reporter is enhanced in the presence of Shh expression plasmid (refer FIG. 8C). Most importantly, this enhanced activity is also sensitive to 5 nM OA treatment. These results suggested a general role for protein phosphatase in the Shh signaling pathway.

Numerous modifications and variations of the present invention are possible in light of the above teachings and, therefore, within the scope of the appended claims, the invention may be practiced otherwise than as particularly described.

---

What is claimed is:

1. A method of identifying a compound that modulates phosphorylation of a transcription factor that functions in a hedgehog signaling pathway comprising:
   a) incubating components comprising the compound, a phosphorylated transcription factor that, when phosphorylated, binds to a hedgehog response element, wherein the hedgehog response element is operatively associated with a target gene, and a phosphatase, under conditions sufficient to allow the components to interact; and
   b) determining a change in the phosphorylation state of the transcription factor as compared to the phosphorylation state of the transcription factor prior to incubating, wherein a change in the phosphorylation state is indicative of a compound that modulates phosphorylation of a transcription factor that functions in a hedgehog signaling pathway.

2. The method according to claim 1, wherein the target gene is chloramphenicol acetyl transferase.

3. The method according to claim 1, wherein the target gene is a lacZ gene.

4. The method according to claim 1, wherein the hedgehog response element is a sonic hedgehog response element.

5. The method of claim 1, wherein the sonic hedgehog response element comprises a nucleic acid having the sequence of SEQ ID NO:1.

6. The method of claim 1, wherein the transcription factor has been identified by:

a) assaying lysate from the cells cultured in media containing an N terminal fragment of a hedgehog polypeptide and identifying as a hedgehog-responsive protein any protein showing induction or increased expression when compared to cells cultured in media not containing the N terminal fragment of a hedgehog polypeptide, b) determining the phosphorylation state of hedgehog-responsive protein identified in step (a) and identifying as a differentially phosphorylated hedgehog-responsive protein any hedgehog-responsive protein that is phosphorylated or dephosphorylated in response to the presence of an N terminal fragment of a hedgehog polypeptide, c) determining whether differentially phosphorylated hedgehog-responsive protein identified in step (d) binds to a hedgehog response element in either its phosphorylated or dephosphorylated state, and d) identifying as a hedgehog-mediated phosphorylation state-dependent transcription factor any differentially phosphorylated hedgehog-responsive protein factor which binds to a hedgehog response element in either its phosphorylated or dephosphorylated state.

7. The method of claim 1, wherein the change in phosphorylation state of the transcription factor causes an increase or decrease in expression of the target gene.

* * * * *